United States Patent [19]

Sohda et al.

[11] Patent Number: 5,239,080

[45] Date of Patent: Aug. 24, 1993

[54] OXAZOLE COMPOUNDS AND THEIR USE AS ANTIDIABETIC AND BONE-REDUCTION INHIBITORY AGENTS

[75] Inventors: Takashi Sohda, Takatsuki; Hitoshi Ikeda, Higashiosaka; Yu Momose, Neyagawa, all of Japan

[73] Assignee: Takeda Chemical Industries, Ltd., Osaka, Japan

[21] Appl. No.: 723,675

[22] Filed: Jun. 27, 1991

Related U.S. Application Data

[63] Continuation of Ser. No. 476,315, Feb. 7, 1990, abandoned.

[30] Foreign Application Priority Data

Feb. 8, 1989 [JP] Japan .................................. 1-29203

[51] Int. Cl.$^5$ .............................................. C07D 263/30
[52] U.S. Cl. ..................................... 548/236; 548/235; 544/238; 544/405; 544/133
[58] Field of Search ................. 514/374; 548/235, 236

[56] References Cited

U.S. PATENT DOCUMENTS

| | | | |
|---|---|---|---|
| 3,470,195 | 9/1969 | O'Mant | 548/236 |
| 3,574,228 | 4/1971 | Brown | 548/236 |
| 3,578,671 | 5/1971 | Brown | 548/236 |
| 3,652,575 | 3/1972 | Hutton et al. | 548/236 |
| 4,596,816 | 6/1986 | Meguro | 548/236 |
| 4,602,027 | 7/1986 | Meguro et al. | |
| 4,774,253 | 9/1988 | Machin et al. | 548/236 |
| 4,775,687 | 10/1988 | Meguro et al. | 548/236 |
| 5,071,988 | 12/1991 | Failli | 548/236 |

FOREIGN PATENT DOCUMENTS

| | | | |
|---|---|---|---|
| 0382199 | 8/1990 | European Pat. Off. | 548/235 |
| 0082369 | 12/1986 | Japan | 548/235 |
| 1206403 | 9/1970 | United Kingdom . | |
| 1292603 | 10/1972 | United Kingdom . | |

OTHER PUBLICATIONS

Burger, ed. "Medicinal Chemistry" 2nd Ed. Interscience, N.Y., (1960) pp. 42 and 497.

Meguro et al, Chem. Abstr. vol. 106 (No. 17) entry 138436k (1987) abstracting Kokai 61,286,376.

K. Brown et al., Chemical Abstracts 73(3):14833t (1970).

A. I. Meyers et al., Chemical Abstracts 81(17):104700s (1974).

J. P. Lokensgard et al., Chemical Abstracts 86(21):155552f (1977).

H. H. Wasserman et al., Chemical Abstracts 95(13):114742K (1981).

L. N. Pridgen et al., Chemical Abstracts 102(3):24527c (1985).

L. N. Lendon et al., Chemical Abstract 102 (3): 24257c (1985).

*Primary Examiner*—Donald G. Daus
*Attorney, Agent, or Firm*—Wegner, Cantor, Mueller & Player

[57] ABSTRACT

Oxazole compounds having the formula:

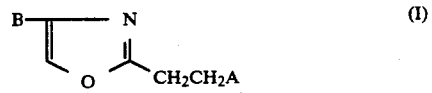

in which A is a group of the formula —$CH_2OR^3$ ($R^3$ is a hydrogen atom, an optionally substituted hydrocarbon residue, an optionally substituted heterocyclic group or an acyl group), or an aldehyde group and B is an optionally substituted phenyl group, or their salts, which are useful as antidiabetic agents.

7 Claims, No Drawings

OXAZOLE COMPOUNDS AND THEIR USE AS ANTIDIABETIC AND BONE-REDUCTION INHIBITORY AGENTS

This application is a continuation of U.S. application Ser. No. 07/476,315 filed Feb. 7, 1990 now abandoned.

BACKGROUND OF THE INVENTION

1. Field of the Invention

This invention relates to oxazole compounds. More particularly, it relates to oxazole compounds which possess activity for lowering blood sugar and activity for improving glucose tolerance and thus are useful as antidiabetic agents.

2. Prior Arts

Various compounds have been prepared to provide antidiabetic agents, which however leave the problem to be improved on both points of activity and side-effect.

4,5-Diaryloxazole-2-alkanoic acid derivatives which show antiinflammatory activity have been known (see U.S. Pat. No. 3,578,671 and Japanese Patent Publication No. Sho 49(1974)-38268).

As the result of studies on 4-aryloxazole compounds, we now prepared new 4-aryloxazole compounds having a substituent at the 2-position which were found to possess activities for lowering blood sugar and improving glucose tolerance.

SUMMARY OF THE INVENTION

This invention, provides an oxazole compound having the formula (I):

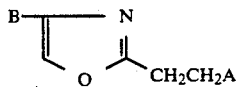

in which A is a group of the formula —$CH_2OR^3$ ($R^3$ is a hydrogen atom, an optionally substituted hydrocarbon residue, an optionally substituted heterocyclic group or an acyl group), or an aldehyde group and B is an optionally substituted phenyl group, or its salt; and an antidiabetic composition which comprises an oxazole compound having the formula (I'):

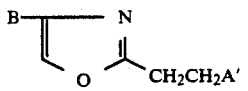

in which A' is a group of the formula —$CH_2OR^{3'}$ ($R^{3'}$ is a hydrogen atom, an optionally substituted hydrocarbon residue, an optionally substituted heterocyclic group or an acyl group), an aldehyde group or an optionally esterified or amidated carboxyl group, and B is an optionally substituted phenyl group, or its salts.

In the above mentioned formulae (I) and (I'), suitable examples of substituents in the optionally substituted phenyl group of B are a halogen, nitro, cyano, an alkoxy which may be substituted or an alkyl which may be substituted. One to four, preferably one or two, the same of different, of these substituents may be substituted on the benzene ring. The halogen includes fluorine, chlorine, bromine and iodine, among which fluorine and chlorine are preferable.

Examples of the alkoxy groups in the alkoxy group which may be substituted, are straight or branched chain alkoxy groups preferably having 1-10 carbon atoms and more preferably having 1-6 carbon atoms, such as methoxy, ethoxy, propoxy, butoxy, tert-butoxy, pentyloxy, hexyloxy, heptyloxy and nonyloxy.

Examples of the alkyl groups in the alkyl group which may be substituted, are straight or branched chain alkyl groups preferably having 1-10 carbon atoms and more preferably having 1-6 carbon atoms, such as methyl, ethyl, propyl, isopropyl, butyl, isobutyl, sec-butyl, tert-butyl, pentyl, isopentyl, neopentyl, hexyl, heptyl, octyl, nonyl or decyl, and cyclic alkyl groups preferably having 3-7 carbon atoms, such as cyclopropyl, cyclobutyl, cyclohexyl or cycloheptyl.

Examples of the substituents on the substituted alkyl or alkoxy groups are a halogen such as fluorine, chlorine, bromine or iodine, hydroxy or a $C_{1-6}$alkoxy such as methoxy, ethoxy, propoxy, isopropoxy, butoxy, pentyloxy or hexyloxy. The number of the substituent is preferably one to three. When its number is two or more, the substituents may be the same or different.

Specifically, the substituted alkoxy group may be trifluoromethoxy, difluoromethoxy, 2,2,2-trifluoroethoxy, 1,1-difluoroethoxy, 1,1-difluoropropoxy and 2,2,3,3-tetrafluorobutoxy.

Also, the substituted alkyl group may be trifluoromethyl, trifluoroethyl, difluoromethyl, trichloromethyl, hydroxymethyl, 1-hydroxyethyl, 2-hydroxyethyl, methoxymethyl, ethoxymethyl, 2-methoxyethyl, 2,2-dimethoxyethyl and 2,2-diethoxyethyl.

The hydrocarbon residue in the optionally substituted hydrocarbon residue of $R^3$ and $R^{3'}$ includes an alkyl, aralkyl, alkenyl and aromatic groups. The alkyl group as mentioned here may be a straight or branched chain alkyl having 1-10 carbon atoms and preferably having 1-6 carbon atoms, specifically such as methyl, ethyl, propyl, isopropyl, butyl, isobutyl, sec-butyl, tert-butyl, pentyl, isopentyl, neopentyl, hexyl, heptyl, octyl, nonyl or decyl, or a cyclic alkyl preferably having 3-7 carbon atoms such as cyclopropyl, cyclobutyl, cyclopentyl, cyclohexyl or cycloheptyl. The aralkyl group may be a phenyl-$C_{1-4}$alkyl such as benzyl, phenethyl or 3-phenylpropyl. The alkenyl group may be preferably a straight or branched chain or cyclic alkenyl having 2-10 carbon atoms, such as allyl, vinyl, crotyl, 2-penten-1-yl, 3-penten-1-yl, 2-hexen-1-yl, 3-hexen-1-yl, 2-cyclopentenyl, 2-cyclohexenyl, 2-methyl-2-propen-1-yl or 3-methyl-2-buten-1-yl. The aromatic group may be a $C_{6-14}$aryl such as phenyl, naphthyl, anthryl or phenanthryl.

Examples of the heterocyclic groups in the optionally substituted heterocyclic group of $R^3$ and $R^{3'}$ include a 5-7 membered heterocycle containing one sulfur, nitrogen or oxygen atom; a 5 or 6 membered heterocycle containing two to four nitrogen atoms, and a 5 or 6 membered heterocycle containing one or two nitrogen atoms and one sulfur or oxygen atom, which may be condensed with a 6 membered ring containing two or less nitrogen atom, benzene ring or a 5 membered ring containing one sulfur atom. Specifically, the heterocyclic group may be 2-pyridyl, 3-pyridyl, 4-pyridyl, pyrimidyl, pyrazinyl, pyridazinyl, pyrazolyl, imidazolyl, thiazolyl, isothiazolyl, oxazolyl, isoxazolyl, pyrido[2,3-d]pyrimidyl, benzopyranyl, 1,8-naphthyridyl 1,5-naphthyridyl, 1,6-naphthyridyl, 1,7-naphthyridyl, quinolyl, thieno[2,3-b]pyridyl, tetrazolyl, thiadiazolyl, oxadiazolyl, triazinyl, triazolyl, thienyl, pyrrolyl, pyrrolinyl, furyl, pyrrolidinyl, benzothienyl, indolyl, imidazolidinyl, piperidyl, piperidino, piperazinyl, morpholinyl or morpholino.

Examples of the acyl groups of $R^3$ and $R^{3'}$ are the hydrocarbon residues of $R^3$ combined with carbonyl or sulfonyl group.

The esterified carboxyl groups of A' are e.g., a group of the formula —$COOR^4$ ($R^4$ is an ester residue). Examples of the ester residues of $R^4$ are the optionally substituted hydrocarbon residues or optionally substituted heterocyclic groups as mentioned with respect to $R^3$. These residues or groups may be substituted by one to three of a halogen, a $C_{1-4}$ alkoxy or the like.

Examples of the amidated carboxyl groups of A' are the group of the formula —$CON(R^5)(R^6)$ in which $R^5$ and $R^6$ are, the same or different, a hydrogen atom, an optionally substituted hydrocarbon residue or an optionally substituted heterocyclic group.

To the optionally substituted hydrocarbon residues or optionally substituted heterocyclic groups of $R^5$ or $R^6$ are applicable those mentioned with respect to $R^3$ and $R^{3'}$. These residues or groups may be substituted by one to three of a halogen, a $C_{1-4}$ alkoxy or the like.

Examples of substituents on the optionally substituted alkyl group mentioned as one group of the optionally substituted hydrocarbon residues with respect to $R^3$, $R^{3'}$, $R^4$, $R^5$ and $R^6$ are a halogen atom (e.g., fluorine, chlorine, bromine or iodine), hydroxy group, a $C_{1-6}$ alkoxy group, an amino group which may be substituted by a $C_{1-6}$ alkyl or a $C_{1-10}$ acyl (e.g., dimethylamino, diethylamino, dipropylamino, acetylamino, propionylamino or benzoylamino), a carbamoyl group which may be substituted by a $C_{1-6}$ alkyl (e.g., dimethylcarbamoyl, diethylcarbamoyl or dipropylcarbamoyl), a $C_{1-6}$ alkoxycarbonyl group (e.g., methoxycarbonyl, ethoxycarbonyl or propoxycarbonyl) or the heterocycle group mentioned above.

Specifically, the substituted alkyl groups of $R^3$, $R^{3'}$ and $R^4$ may be trifluoromethyl, trifluoroethyl, difluoromethyl, trichloromethyl, 2-hydroxyethyl, 2-methoxyethyl, 2-ethoxyethyl, 2,2-dimethoxyethyl, 2,2-diethoxyethyl, 2-pyridylmethyl, 3-pyridylmethyl, 4-pyridylmethyl, 2-(2-thienyl)ethyl, 3-(3-furyl)propyl, 2-morpholinoethyl, 3-pyrrolylbutyl, 2-piperidinoethyl, 2-(N,N-dimethylamino)ethyl, 2-(N-methyl-N-ethylamino)ethyl, 2-(N,N-diisopropylamino)ethyl, 5-(N,N-dimethylamino)pentyl, N,N-dimethylcarbamoylethyl, N,N-dimethylcarbamoylpentyl, ethoxycarbonylmethyl, isopropoxycarbonylethyl or tert-butoxycarbonylpropyl.

Examples of substituents on the optionally substituted aralkyl mentioned as one group of the optionally substituted hydrocarbon groups of $R^3$, $R^{3'}$, $R^4$, $R^5$ and $R^6$ are a halogen atom (e.g., fluorine, chlorine, bromine or iodine), a $C_{1-6}$ alkoxy group, a $C_{1-6}$ alkyl group, a halogenated $C_{1-6}$ alkyl group substituted by the above halogen (e.g., trifluoromethyl, difluoromethyl, 2,2,2-trifluoroethyl or 2,2,2-trichloroethyl) or an amino group which may be substituted by a $C_{1-6}$ alkyl or a $C_{1-10}$ acyl (e.g., methylamino, dimethylamino, diethylamino, dibutylamino, propionylamino, acetylamino or benzoylamino).

Specifically, the substituted aralkyl group of $R^3$, $R^{3'}$, $R^4$, $R^5$ and $R^6$ may be 4-chlorobenzyl, 3-(2-fluorophenyl)propyl, 3-methoxybenzyl, 3,4-dimethoxyphenethyl, 4-ethylbenzyl, 4-(3-trifluoromethylphenyl)-butyl, 4-acetylaminobenzyl or 4-dimethylaminophenethyl.

Examples of substituents on the optionally substituted aromatic group mentioned as the optionally substituted hydrocarbon residue of $R^3$, $R^{3'}$, $R^4$, $R^5$ and $R^6$ are a halogen atom (e.g., fluorine, chlorine, bromine or iodine), a $C_{1-6}$ alkyl group, a halogenated $C_{1-6}$ alkyl group substituted by the above mentioned halogen, hydroxy group, a $C_{1-6}$ alkoxy group, a $C_{1-10}$ acyl group, an amino group which may be substituted by a $C_{1-6}$ alkyl or a $C_{1-10}$ acyl (e.g., dimethylamino, diethylamino, dipropylamino, acetylamino, propionylamino or benzoylamino), a carbamoyl group which may be substituted by a $C_{1-6}$ alkyl (e.g., dimethylcarbamoyl, diethylcarbamoyl or dipropylcarbamoyl), a $C_{1-6}$ alkoxycarbonyl group (e.g., methoxycarbonyl, ethoxycarbonyl or propoxycarbonyl) or the above mentioned heterocyclic group. The number of the substituents is preferably one to three. When the number is two or more, the substituents may be the same or different.

Specifically, the substituted aromatic groups of $R^3$, $R^{3'}$ and $R^4$ may be 4-chlorophenyl, 4-cyclohexylphenyl, 5,6,7,8-tetrahydro-2-naphthyl, 3-trifluoromethylphenyl, 4-hydroxyphenyl, 3,4,5-trimethoxyphenyl, 6-methoxy-2-naphthyl, 4-(4-chlorobenzyloxy)phenyl, 3,4-methylenedioxyphenyl, 4-(2,2,2-trifluoroethoxy)phenyl, 4-propionylphenyl, 4-cyclohexancarbonylphenyl, 4-dimethylaminophenyl, 4-benzoylaminophenyl, 4-diethylcarbamoylphenyl or 4-tert-butoxycarbonylphenyl.

Examples of substituents on the optionally substituted heterocyclic group of $R^3$, $R^{3'}$, $R^4$, $R^5$ and $R^6$ are a halogen (e.g., fluorine, chlorine, bromine or iodine), a $C_{1-6}$ alkyl, a halogenated $C_{1-6}$ alkyl group substituted by the above mentioned alkyl, a hydroxy group, a $C_{1-6}$ alkoxy group, a $C_{1-10}$ acyl group, an amino group which may be substituted by a $C_{1-6}$ alkyl or a $C_{1-10}$ acyl (e.g., dimethylamino, diethylamino, dipropylamino, acetylamino, propionylamino or benzoylamino), a carbamoyl group which may be substituted by a $C_{1-6}$ alkyl (e.g., dimethylcarbamoyl, diethylcarbamoyl, or dipropylcarbamoyl), a $C_{1-6}$ alkoxycarbonyl (e.g., methoxycarbonyl, ethoxycarbonyl or propoxycarbonyl) or the above mentioned heterocyclic group.

Specifically, the substituted heterocyclic group of $R^3$, $R^{3'}$ and $R^4$ may be 5-chloro-2-pyridyl, 3-methoxy-2-pyridyl, 5-methyl-2-benzothiazolyl, 5-methyl-4-phenyl-2-thiazolyl, 3-phenyl-5-isoxazolyl, 4-(4-chlorophenyl)-5-methyl-2-oxazolyl, 3-phenyl-1,2,4-thiadiazol-5-yl, 5-methyl-1,3,4-thiadiazol-2-yl, 5-acetylamino-2-pyrimidyl, 2-methyl-2-thienyl, 4,5-dimethyl-2-furyl, of 4-methyl-2-morpholinyl.

The number of the substituents on the optionally substituted alkyl, aralkyl, aromatic or heterocyclic group as mentioned above is preferably one to three. When its number is two or more, the substituents may be the same or different.

The object compounds of the invention can be prepared by any one of the following methods. Raw materials to be used in the methods can be prepared by known methods or analogous ones thereto.

Method A

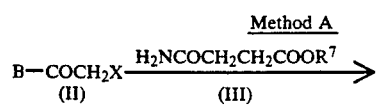

-continued

Method A

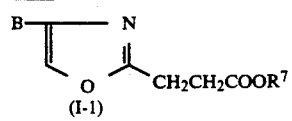
(I-1)

In the formulas, B has the same meaning as defined above, $R^7$ is a lower alkyl or aralkyl group and X is a leaving group.

Method B

Step 1

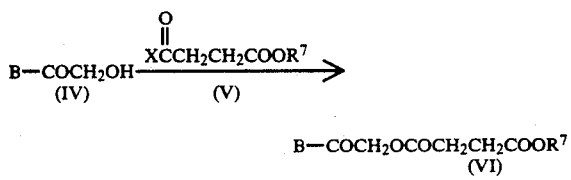

Step 2

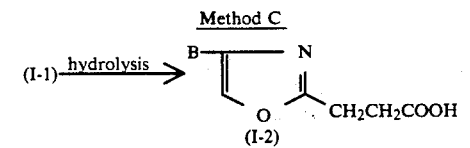

Method C

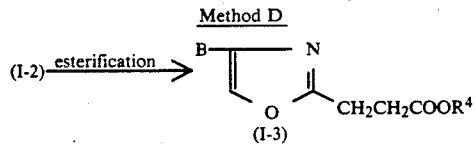

Method D

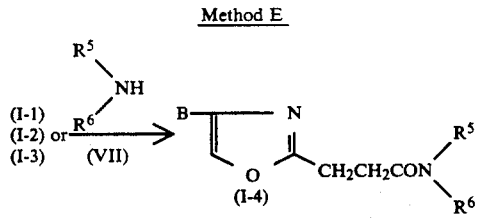

Method E

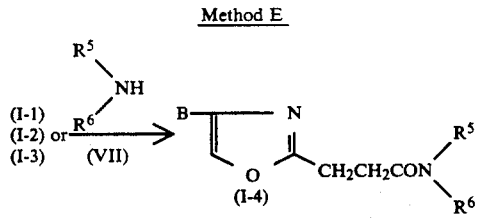

Method F

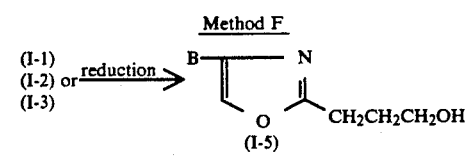

Method G

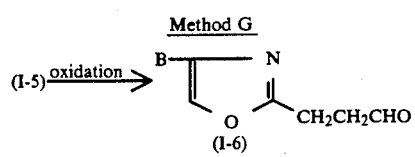

Method H

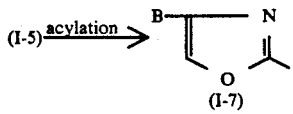
(I-7)

In the formula, B has the same meaning as defined above and $R^8$ is a hydrocarbon residue.

Method I

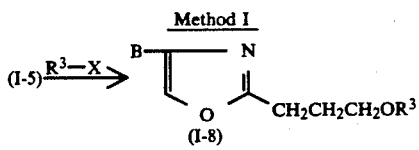

Method J

Step 1

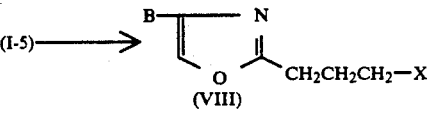

Step 2

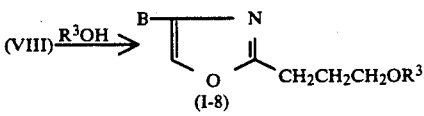

In the above formulae of Methods B–G, I, J, the symbols are as defined before.

In the above formula, the hydrocarbon residues of $R^8$ mean the same ones as illustrated with respect to the above $R^3$, $R^4$, $R^5$ and $R^6$. The leaving groups of X may be a halogen (e.g., chlorine, bromine or iodine) or substituted sulfonyloxy (e.g., mesyloxy, tosyloxy or benzenesulfonyloxy). The lower alkyl groups of $R^7$ may be methyl, ethyl, propyl or butyl.

Details of each the methods are as follows.

Method A

The compound (II) or salt thereof is reacted with a succinamic acid ester (III) to afford the compound (I-1) or salt thereof. The reaction can be conducted without solvent or in the presence of an inert solvent. Examples of the inert solvents are toluene, xylene, pyridine, 1,2-dichloroethane, 1,1,2,2-tetrachloroethane, N,N-dimethylformamide or dimethyl-sulfoxide.

The reaction temperature is about 30°–200° C., preferably 60°–150° C. and the reaction time is about 30 minutes to 10 hours. The compound (III) is used in about 1 to 10 moles, preferably about 1.5–4 moles, to one mole of the compound (II) or salt thereof.

Method B

Step 1

Firstly, the compound (IV) or salt thereof is acylated with a succinic acid monohalide (V) to afford the compound (IV) or salt thereof. The acylation can be conducted in accordance with a method known per se. For instance, it can be conducted in the presence of a base in an inert solvent. Examples of the inert solvents are chloroform, dichloromethane, ethyl acetate, tetrahydrofuran, water or a mixture thereof. Examples of the bases are triethylamine, pyridine, N-methylmorpholine, sodium hydrogen carbonate, potassium hydrogen carbonate, sodium carbonate or potassium carbonate. Such triethylamine or pyridine can be served as the solvent.

The reaction temperature is about −10°−+50° C. and the reaction time is about 10 minutes–5 hours. The compound (V) or salt thereof is used in about 1–1.2 moles, to one mole of the compound (IV).

Step 2

The compound (VI) or salt thereof is subjected to a cyclization to convert into the compound (I-1) or salt thereof. The compound (I-1) or salt thereof is prepared by cyclizing the compound (VI) or salt thereof with a nitrogen-containing cyclizing agent, e.g., urea or ammonia [see J. Org. Chem., Vol 25, p.1151]. In the case of using ammonia, it is preferably in the form of ammonium salt such as ammonium acetate in acetic acid. The reaction can be conducted in an inert solvent as described in Step 1. The nitrogen-containing clyclizing agent is used in about 0.5–10 mole, to one mole of the compound (VI) or salt thereof. The reaction temperature is about 10°–150° C., and the reaction time is about 30 minutes to 6 hours.

Method C

The compound (I-2) or salt thereof can be prepared by hydrolyzing the compound (I-1) or salt thereof which was prepared by Methods A and B. The hydrolysis can be conducted in the presence of an acid or base in an aqueous solvent, in accordance with the conventional methods.

Examples of the solvents to be usable include a mixture of water with an organic solvent, e.g., alcohols such as methanol or ethanol; ethers such as tetrahydrofuran or dioxane; N,N-dimethylformamide, dimethylsulfoxide or acetone.

Examples of the bases include potassium carbonate, sodium carbonate, sodium methoxide, sodium ethoxide, potassium tert-butoxide, sodium hydroxide, potassium hydroxide or lithium hydroxide. Examples of the acids are hydrochloric acid, sulfuric acid, acetic acid or hydrobromic acid. The acid or base is preferably used in an excess amount, about 1.2–6 equivalents of base or about 2–50 equivalents of acid to the compound (I-1) or salt thereof. Usually, the reaction temperature is about −20° C.−+150° C., preferably about −10° C.−+100° C. and the reaction time is about 10 minutes to 20 hours.

Method D

The compound (I-3) or salt thereof can be prepared by esterification of the compound (I-2) or salt thereof. The esterification can be conducted in accordance with the method known per se. For example, the compound (I-2) or salt thereof is directly reacted with an alcohol (R$^4$OH) in the presence of an acid or with R$^4$X in the presence of a base. Alternatively, a reactive derivative of the compound (I-2) e.g., the acid anhydride, acid halide (such as acid chloride or acid bromide), imidazolide or mixed anhydride (such as anhydride with methyl carbonate, ethyl carbonate or isobutyl carbonate) is reacted with the alcohol (R$^4$OH). The acids or bases as mentioned in Method C are applicable to the above reaction. The reaction can be conducted in a similar way to Method E mentioned below (a method for using acid halide). Furthermore, the compound (I-3) or salt thereof can be also prepared by reacting the compound (I-2) or salt thereof with a diazo compound (e.g., diazomethane or diphenyldiazomethane).

Method E

The compound (I-4) or salt thereof can be prepared by amidating the compound (I-1), (I-2) or (I-3), or salt thereof. The amidation can be conducted by reacting the compound (I-1) or (I-3) or salt thereof with an amine derivative (VII) or salt thereof in an inert solvent (e.g., ethanol, propanol, toluene, xylene, pyridine, 1,2-dichloroethane, 1,1,2,2-tetrachloroethane, N,N-dimethylformamide, or dimethyl sulfoxide) or in the absence of any solvent. The reaction temperature is about 20°–200° C., and the reaction time is about 10 minutes to 10 hours. The amine derivative (VII) or salt thereof is preferably used in an excess amount, to the compound (I-1) or (I-3) or salt thereof. The reaction of the compound (I-2) or salt thereof with the amine derivative (VII) can be conducted by the methods known per se. For instance, there are a method for directly condensing the compound (I-2) or salt thereof and the amine derivative (VII) or salt thereof in the presence of dicyclohexylcarbodiimide or the like, or a method for reacting a reactive derivative of the compound (I-2) or salt thereof (e.g., acid anhydride, acid halide such as acid chloride or acid bromide, imidazolide or mixed anhydride such as anhydride with methyl carbonate, ethyl carbonate or isobutyl carbonate), with the amine derivative (VII) or salt thereof. Among these methods, the most convenient one is to use an acid halide or mixed anhydride of the compound (I-2). In case of using the acid halide, the reaction is preferably conducted in a conventional solvent (e.g., chloroform, dichloromethane, ethyl acetate, tetrahydrofuran or water, or mixture thereof) in the presence of a base (e.g., triethylamine, N-methylmorpholine, sodium hydrogen carbonate, potassium hydrogen carbonate, sodium carbonate or potassium carbonate). The amine derivative (VII) or salt thereof is used in about 1–1.2 moles, to one mole of the compound (I-2) or salt thereof. The reaction temperature is preferably −10° C. −+30° C., and the reaction time is about 30 minutes to 10 hours. In case of using the mixed anhydride, the compound (I-2) or salt thereof is reacted with a chlorocarbonate (e.g., methyl chlorocarbonate, ethyl chlorocarbonate or isobutyl chlorocarbonate) in the presence of a base (e.g., triethylamine, N-methylmorpholine, sodium hydrogen carbonate, potassium hydrogen carbonate, sodium carbonate or potassium carbonate). The reaction is conducted in an inert solvent (e.g., chloroform, dichloromethane, ethyl acetate, tetrahydrofuran, water or mixture thereof). The reaction temperature is preferably −10° C.−+30° C. The amine derivative (VII) is used in about 1–1.2 moles, to one mole of the compound (I-2).

Method F

The reduction can be conducted in accordance with the methods known per se, e.g., the reduction with a metallic hydride compound, a metallic hydrogen complex, diborane or a substituted diborane, or a catalytic hydrogenation. (refer to "SHIN JIKKEN-KAGAKUKOZA (New Experimental Chemistry Handbook)" Vol. 15 (II) (1976) edited by The Chemical Society of Japan and issued by Maruzen Publishing Co., Ltd of Japan)

That is, the reaction is conducted by treating the compound (I-1), (I-2) or (I-3), or salt thereof with a reducing agent.

Suitable examples of the reducing agents are metallic hydride complexes such as alkali metal boron hydrides (e.g., sodium borohydride or lithium borohydride) or lithium aluminum hydride; metal hydride compounds such as sodium hydride; metals or metal salts such as organic tin compounds (e.g., triphenyltin hydride), nickel compounds or zinc compounds; catalytic reducing agents using transition metal catalysts and hydrogen, and diborane compounds.

The reduction is conducted in an organic solvent which does not impede it. Examples of the solvents are aromatic hydrocarbons such as benzene, toluene or xylene; halogenated hydrocarbons such as chloroform, dichloromethane, 1,2-dichloroethane or 1,1,2,2-tetrachloroethane; ethers such as diethyl ether, dioxane, tetrahydrofuran or ethylene glycol monomethylether; alcohols such as methanol, ethanol or propanol; amides such as dimethylformamide, or mixture thereof, which are suitably selected in accordance with the kind of the reducing agent.

The reaction temperature is about 0°–130° C., especially 10°–100° C., and the reaction time is about 1–24 hours.

Method G

The oxidation can be conducted in accordance with the methods known per se, e.g., the oxidation with manganese dioxide, chromic acid (e.g., chromium oxide (VI)-pyridine) or dimethyl sulfoxide (refer to "SHIN JIKKENKAGAKU KOZA (New Experimental Chemistry Handbook)", Vol. 15 (I-1) and (I-2) (1976) edited by The Chemical Society of Japan and issued by Maruzen Publishing Co., Ltd. of Japan).

For instance, the oxidation with dimethyl sulfoxide is conducted in an inert solvent such as chloroform, dichloromethane, benzene or toluene in the coexistence of an electrophilic agent such as acetic anhydride, phosphoric anhydride, dicyclohexylcarbodiimide or chlorine. Dimethyl sulfoxide is used in 1–5 equivalents, preferably 1–2 equivalents, to the compound (I-5). The electrophilic agent is used in an equivalent, to dimethyl sulfoxide. The reaction temperature is about $-20°-+60°$ C., preferably about 0°–40° C. The reaction time is about 0.5–50 hours, preferably about 1–20 hours.

Method H

The acylation can be conducted by the methods known per se, e.g., to react the compound (I-5) directly with the carboxylic acid ($R^8$—COOH) in the presence of a condensing agent (e.g., cyclohexylcarbodiimide) or to react the compound (I-5) with a reactive derivative of the carboxylic acid ($R^8$—COOH) such as the acid anhydride, acid halide (e.g., acid chloride or acid bromide), imidazolide or mixed anhydride (e.g., anhydride with methyl carbonate, ethyl carbonate or isobutyl carbonate). The most convenient method is to use the acid halide or mixed anhydride of $R^8$—COOH.

In the case of the acid halide, the reaction is usually conducted in a solvent (e.g., chloroform, dichloromethane, ethyl acetate, tetrahydrofuran, or water, or mixture thereof) in the presence of a base (e.g., triethylamine, N-methylmorpholine, sodium hydrogen carbonate, potassium hydrogen carbonate, sodium carbonate or potassium carbonate). The reaction temperature is about $-10°-+50°$ C. The carboxylic acid ($R^8$—COOH) is used in 1–1.2 moles to one mole of the compound (I-5) or salt thereof.

In the case of the mixed anhydride, it is formed by reacting $R^8$—COOH with a chlorocarbonate (e.g., methyl chlorocarbonate, ethyl chlorocarbonate or isobutyl chlorocarbonate), in the presence of a base (e.g., triethylamine, N-methylmorpholine, sodium hydrogen carbonate, potassium hydrogen carbonate, sodium carbonate or potassium carbonate). The reaction is conducted in an inert solvent (e.g., chloroform, dichloromethane, ethyl acetate, tetrahydrofuran, water or mixture thereof). The reaction temperature is about $-10°-+30°$ C., and the reaction time is about 0.5–50 hours. The carboxylic acid ($R^8$—COOH) is used in about 1–1.2 moles, to one mole of the compound (I-5).

Method I

In this method, the compound (I-5) or salt thereof is reacted with $R^3$-X in the presence of a base (e.g., sodium hydride, potassium hydride, sodium amide, triethylamine, N-methylmorpholine, sodium hydrogen carbonate, potassium hydrogen carbonate, sodium carbonate or potassium carbonate), thereby affording the compound (I-8). The reaction is conducted in an inert solvent (e.g., tetrahydrofuran, dioxane, diethyl ether, toluene, xylene, benzene, 1,2-dichloroethane, 1,1,2,2-tetrachloroethane, N,N-dimethylformamide or dimethyl sulfoxide). The reaction temperature is about $-20°-100°$ C., preferably $-10°-50°$ C., and the reaction time is about 0.5–20 hours. $R^3$—X is used in an excess amount, to the compound (I-5) or salt thereof.

Method J

Step 1

The compound (VIII) is prepared by reacting the compound (I-5) or salt thereof with a halogenating agent or a sulfonylating agent. Suitable examples of the halogenating agents are thionyl chloride or phosphorus tribromide. The use of such halogenating agent can produce the compound (VIII), X being chlorine or bromine, or salt thereof. The halogenation is conducted in an inert solvent (e.g., benzene, toluene, xylene, chloroform or dichloromethane) or using an excess amount of the halogenating agent to serve as solvent. The reaction temperature is about 10°–80° C. The halogenating agent is used in about 1–20 moles, to one mole of the compound (I-5) or salt thereof. Suitable examples of the sulfonylating agents are mesyl chloride, tosyl chloride or benzenesulfonyl chloride, thereby affording the compound (VIII), X being mesyloxy, tosyloxy or benzensulfonyoxy, respectively, or salt thereof. The sulfonylation is conducted in an inert solvent (e.g., benzene, toluene, xylene, diethylether, ethyl acetate, tetrahydrofuran, chloroform or dichloromethane), preferably in the presence of a base (e.g., triethylamine, N-methylmorpholine, sodium hydrogen carbonate, potassium hydrogen carbonate, sodium carbonate or potassium carbonate). The reaction temperature is about 0°–130° C., preferably 10°–100° C. The reaction time is about 10 minutes to 5 hours. Each of the sulfonylating agent and the base is used in about 1–1.2 moles, to one mole of the compound (I-5) or salt thereof. The compound (VIII), X being iodine, or salt thereof can be prepared by reacting one mole of the compound (VIII), X being bromine, iodine or sulfonyloxy, or salt thereof as thus obtained, with 1–3 moles of sodium iodide or potassium iodide. For this reaction, such solvent as acetone, methylethyl ketone, diethyl ether, tetrahydrofuran or dioxane is usable. The reaction temperature is about 20°–80° C.

Step 2

Subsequently, the compound (VIII) or salt thereof is reacted with an alcohol ($R^3$—OH) to prepare the compound (I-8) or salt thereof. The reaction is usually conducted in an inert solvent (e.g., diethyl ether, choroform, dichloromethane, ethyl acetate, tetrahydrofuran, dioxane or N,N-dimethylformamide) in the presence of a base (e.g., triethylamine, N-methyl-morpholine, sodium hydrogen carbonate, potassium hydrogen carbonate, sodium carbonate or potassium carbonate). The reaction temperature is about 0°-100° C., and the reaction time is about 5 minutes to 10 hours. The alcohol ($R^3$—OH) is used in about 1-3 moles, to one mole of the compound (VIII) or salt thereof.

The salts of the compounds to be employed in the above mentioned Methods A-J are similar ones to the salts of the compounds (I) and (I').

The compounds or their salts thus obtained can be isolated and purified, e.g., by a conventional method such as filtration, concentration, concentration under reduced pressure, extraction with solvent, redistribution, change of basicity, crystallization, recrystallization, distillation, sublimation, salting out or chromatography.

When the compound (I) or (I') has an acidic functional group (e.g., free carboxyl group), its salt with a pharmaceutically acceptable base may be formed in accordance with the conventional method. Examples of such salts are the sodium, potassium, aluminum and calcium salts. When the compound (I) or (I') has a basic functional group, its salt with a pharmaceutically acceptable acid may be formed in accordance with the conventional method. Examples of such salts are the hydrochloric acid, sulfuric acid, acetic acid and fumaric acid salts.

As for toxicity of the compounds (I) and (I'), and salt thereof, with death was observed on the compounds prepared, e.g., by Examples 37 and 39 when orally administered in 300 mg/kg to mice.

The compounds (I) and (I') and salts thereof possess blood sugar lowering activity or glucose tolerance improving activity in mammals (e.g., mouse, rat, rabbit, dog, cat, cow, pig and human being) and their toxicity is very low. Thus, they can be used as therapeutic agent for diabetes of mammals (e.g., mouse, rat, rabbit, dog, cat, cow, pig and human being).

The compounds of the invention can be administered to the human being through any of oral or parental routes.

Compositions for oral administration may be solid or liquid forms, specially tablets (including sugar coated tablets and film coated tablets), pills, granules, powders, capsules (including soft capsules), syrups, emulsions and suspensions. Such compositions will contain conventional carriers or excipients and can be prepared by known methods. Examples of carriers or excipients for tablets are lactose, starch, sucrose and magnesium stearate.

Compositions for parental administration are e.g., injections and suppositories, the former of which includes subcutaneous, intracutaneous, intramuscular or like injections. Such injections can be prepared by dissolving, suspending or emulsifying the compound (I) or (I'), or salt thereof in or with sterile aqueous or eily liquids which are usually employed in injections, in accordance with the methods known in the art. Examples of the aqueous liquids for injections are physiological saline and isotonic solution, which may be used together with a suitable suspending agent such as sodium carboxy methylcellulose or a nonionic surfactant depending upon circumstances. Examples of the oily liquids are sesame oil and soybean oil, which may be used together with a solubilizing agent such as benzyl benzoate or benzyl alcohol. The injections thus prepared are usually put into ampules.

The oral dosage of the compounds (I) or (I'), or salts thereof when used as therapeutic agent for diabetes is 1-500 mg/day/adult, preferably 10-150 mg.

The invention is further illustrated by examples, test examples and preparation examples, by which no limitation shall be given.

EXAMPLE

Example 1

A mixture of 3,5-ditrifluoromethylphenacyl bromide (3.1 g) and ethyl succinamate (5.4 g) was heated for 2 hours at 130° C. The reaction mixture was poured into water. The precipitated crystals were collected by filtration to obtain ethyl 4-(3,5-ditrifluoromethylphenyl)-2-oxazolepropionate (1.7 g, 47%). Recrystallization from hexane gave colorless prism crystals of mp 70°-71° C.

Elementary analysis for $C_{16}H_{13}NO_3F_6$: Calcd. (%): C, 50.40; H, 3.44; N, 3.67; Found (%): C, 50.62; H, 3.40; N, 3.70.

Examples 2-10

By the method of Example 1, the compounds listed in Table 2 were obtained.

Example 11

To a solution of 4-chloro-α-hydroxyacetophenone (4.84 g) in pyridine (50 ml) was added ethyl succinyl chloride (4.8 ml) at room temperature, followed by stirring for 2 hours. The reaction mixture was poured into water and extracted with ethyl acetate. The ethyl acetate layer was washed successively with 6N-HCl and water, and dried over $MgSO_4$. After distilling off the solvent, the oily residue was subjected to a silica gel column chromatography. Crystals (7.85 g, 93%) of 2-(4-chlorophenyl)-2-oxoethyl ethyl succinate were obtained from the fraction eluted with ethyl acetate-hexane (1:2, V/V). Recrystallization from ether-hexane gave colorless needle crystals of mp 50°-51° C.

Elementary analysis for $C_{14}H_{15}O_5Cl$: Calcd.: C, 56.29; H, 5.06; Found: C, 56.55; H, 5.08.

A mixture of 2-(4-chlorophenyl)-2-oxoethyl ethyl succinate (7.6 g), ammonium acetate (9.8 g) and acetic acid (80 ml) was stirred for an hour at 110° C. and refluxed for 2 hours. The solvent was distilled off. The residue was diluted with water, made basic by addition of aqueous sodium hydrogen carbonate solution and then extracted with ethyl acetate. The ethyl acetate layer was washed with water, and dried over $MgSO_4$. After removal of the solvent, the oily residue was subjected to a silica gel column chromatography. Crystals of ethyl 4-(4-chlorophenyl)-2-oxazolepropionate (2.23 g, 31%) were obtained from the fraction eluted with ethyl acetate-hexane (1:3, V/V). Recrystallization from ethyl acetate-hexane gave colorless plate crystals of mp 65°-66° C.

Elementary analysis for $C_{14}H_{14}NO_3Cl$: Calcd. (%): C, 60.11; H, 5.04; N, 5.01; Found (%): C, 59.96; H, 5.07; N, 5.01.

Example 12

Ethyl 4-(3,5-ditrifluoromethylphenyl)-2-oxazolepropionate (1.6 g) was dissolved in methanol (20 ml), to which 10% NaOH (10 ml) was added. After stirring for 10 minutes at room temperature, the mixture was poured into water. The resultant was extracted with ether. The aqueous layer was made acidic with 2N-HCl and the precipitated crystals of 4-(3,5-ditrifluoromethyl-phenyl)-2-oxazolepropionic acid (1.3 g, 87%) were collected by filtration. Recrytallization from ether-hexane gave colorless prism crystals of mp 130°-131° C.

Elementary analysis for $C_{14}H_9NO_3F_6$: Calc. (%): C, 47.61; H, 2.57; N, 3.97; Found (%): C, 47.38; H, 2.53; N, 3.97.

Examples 13-22

By the method of Example 12, the compounds listed in Table 3 were obtained.

Example 23

To a mixture of 4-(4-chlorophenyl)-2-oxazolepropionic acid (0.5 g) and isopropanol (30 ml) was added conc. sulfuric acid (0.3 ml), and the resultant was refluxed for 5 hours. The reaction mixture was poured into water and extracted with ether. The ether layer was washed succesively with a saturated sodium hydrogen carbonate aqueous solution and water, and dried over $MgSO_4$. The ether was distilled off to give crystals of isopropyl 4-(4-chlorophenyl)-2-oxazolepropionate (530 mg, 91%). Recrystallization from hexane gave colorless prism crystals of mp 30°-31° C.

Elementary analysis for $C_{15}H_{16}NO_3Cl$: Calc. (%): C, 61.33; H, 5.49; N, 4.77; Found (%): C, 61.18; H, 5.49; N, 4.77.

Example 24

A mixture of 4-(4-chlorophenyl)-2-oxazolepropionic acid (0.5 g), benzyl bromide (0.25 ml), potassium carbonate (0.33 g) and dimethylformamide (DMF)(10 ml) was stirred for 3 hours at room temperature. The reaction mixture was poured into water to obtain crystals of benzyl 4-(4-chlorophenyl)-2-oxazolepropionate (0.664 g, 98%). Recrystallization from ether-hexane gave colorless prism crystals of mp 66°-67° C.

Elementary analysis for $C_{19}H_{16}NO_3Cl$: Calc. (%): C, 66.77; H, 4.72; N, 4.10; Found (%): C, 66.91; H, 4,69; N, 4.02.

Example 25-27

By the method of Example 24, the compounds listed in Table 4 were obtained.

Example 28

To a solution of 4-(4-chlorophenyl)-2-oxazolepropionic acid (0.7 g) in tetrahydrofuran (THF) (20 ml), were added oxalyl chloride (0.27 ml) and DMF (one drop) at 0° C. After stirring for 2 hours at room temperature, the solvent was distilled off. The oily residue was dissolved in THF (10 ml), to which 3,4,5-trimethoxybenzyl alcohol (1.1 g) and triethylamine (1.2 ml) were added in that order. After stirring for 4 hours at room temperature, the mixture was poured into water and then extracted with ether. The ether layer was washed with water and dried over $MgSO_4$. After distilling off the solvent, the oily residue was subjected to a silica gel column chromatography. Crystals of 3,4,5-trimethoxybenzyl 4-(4-chlorophenyl)-2-oxazolepropionate (0.743 g, 62%) were obtained from the fraction eluted with ethyl acetate-hexane. Recrystallization from dichloromethane-hexane gave colorless prism crystals of mp 86°-87° C.

Elementary analysis for $C_{22}H_{22}NO_6Cl$: Calc. (%): C, 61.19; H, 5.13; N, 3.24; Found (%): C, 61.29; H, 5.12; N, 3.33.

Example 29-31

By the method of Example 28, the compounds listed in Table 5 were obtained.

Example 32

4-Methoxybenzyl 4-(4-chlorophenyl)-2-oxazolepropionate was obtained by the same method as in Example 24. Recrystallization from diethyl ether-hexane gave colorless prism crystals of mp 69°-70° C.

Example 33

To a solution of 4-(4-chlorophenyl)-2-oxazolepropionic acid (0.5 g) in dichloromethane (20 ml) was added diphenyldiazomethane (0.425 g). After stirring for 4 hours at room temperature, acetic acid (0.5 ml) was added to the mixture. The reaction mixture was washed with a saturated sodium hydrogen carbonate aqueous solution and water, and then dried over $MgSO_4$. The solvent was distilled off and then the oily residue was subjected to a silica gel column chromatography. Crystals of diphenylmethyl 4-(4-chlorophenyl)-2-oxazolepropionate (0.759 g, 91%) were obtained from the fraction eluted with ether-hexane (1:3, V/V). Recrystallization from ether-hexane gave colorless prism crystals of mp 94°-95° C.

Elementary analysis for $C_{25}H_{20}NO_3Cl$: Calc. (%): C, 71.85; H, 4.82; N, 3.35; Found (%): C, 71.83; H, 4.79; N, 3.38.

Example 34

To a solution of 4-(4-chlorophenyl)-2-oxazolepropionic acid (0.5 g) in acetonitrile (20 ml) were added 2-phenyl-2-propanol (0.325 g), dicyclohexylcarbodiimide (0.49 g) and 4-dimethylaminopyridine (0.025 g), followed by stirring for 65 hours at room temperature. 2-Phenyl-2-propanol (0.325 g), dicyclohexylcarbodiimide (0.49 g) and 4-dimethylaminopyridine (0.025 g) were further added to the reaction mixture, followed by stirring for 2 hours at 50° C. The reaction mixture was filtered to remove an insoluble substance, and the filtrate was then concentrated. The oily residue was subjected to a silica gel column chromatography. Crystals of 1-methyl-1-phenylethyl 4-(4-chlorophenyl)-2-oxazolepropionate (0.297 g, 38%) were obtained from the fraction eluted with ethyl acetate-hexane (1:4, V/V). Recrystallization from hexane gave colorless prism crystals of mp 94°-95° C.

Elementary analysis for $C_{21}H_{20}NO_3Cl$: Calc. (%): C, 68.20; H, 5.45; N, 3.79; Found (%): C, 68.04; H, 5.47; N, 3.82.

Example 35

To a solution of 4-(4-chlorophenyl)-2-oxazolepropionic acid (0.4 g) in THF (20 ml) were added triethylamine (0.33 ml) and ethyl chlorocarbonate (0.23 ml) at −30° C., followed by stirring for 30 minutes at the same temperature. The mixture was poured into 30% methylamine aqueous solution (10 ml), and the resultant was stirred for 15 minutes at room temperature. The reaction mixture was poured into water and extracted with ethyl acetate. The ethyl acetate layer was washed with water, dried over $MgSO_4$ and concentrated to obtain crystals of N-methyl-4-(4-chlorophenyl)-2-oxazolepropionamide (0.375 g, 89%). Recrystallization from dichloromethane-ethanol gave colorless prism crystals of mp 169°–170° C.

Elementary analysis for $C_{13}H_{13}N_2O_2Cl$: Calc. (%): C, 58.99; H, 4.95; N, 10.58; Found (%): C, 58.73; H, 4.84; N, 10.46.

Example 36

By the method of Example 35, crystals of N-benzyl-N-methyl-4-(4-chlorophenyl)-2-oxazolepropionamide (yield: 71%) was obtained. Recrystallization from dicloromethane-ethanol gave colorless prism crystals of mp 99°–100° C.

Elementary analysis for $C_{20}H_{19}N_2O_2Cl$: Calc. (%): C, 67.70; H, 5.40; N, 7.89; Found (%): C, 67.82; H, 5.38; N, 7.84.

EXAMPLE 37

To a solution of 4-(4-chlorophenyl)-2-oxazolepropionic acid (1.5 g) in THF (20 ml) was added lithium aluminum hydride (0.27 g), followed by stirring for 3 hours at room temperature. Water (3 ml) was added to the reaction mixture. The resultant was extracted with ethyl acetate. The ethyl acetate layer was washed with 2N-HCl and water, dried over MgSO4, and distilled to remove the solvent. The oily residue was subjected to a silica gel chromatography. Crystals of 3-[4-(4-chlorophenyl)-2-oxazolyl]propanol (1.11 g, 78%) were obtained from the fraction eluted with ethyl acetatehexane (2:1, V/V). Recrystallization from ether-hexane gave colorless prism crystals of mp 43°–44° C.

Elementary analysus for $C_{12}H_{12}NO_2Cl$: Calc. (%): C, 60.64: H, 5.09: N, 5.89; Found (%): C, 60.44; H, 5.06; N, 5.82.

Examples 38–39

By the method of Example 37, the compounds listed in Table 6 were obtained.

Example 40

To a solution of ethyl 4-phenyl-2-oxazolepropionate (1.4 g) in THF (20 ml) was added sodium borohydride (0.86 g). Methanol (4 ml) was dropwise added to the mixture over a period of 10 minutes under reflux. The reaction mixture was refluxed for further 30 minutes, concentrated, made acidic and then extracted with ethyl acetate. The ethyl acetate layer was washed with water, dried over MgSO4, and distilled to obtain crystals of 3-(4-phenyl-2-oxazolyl)propanol (1.07 g, 92%). Recrystallization from ether-hexane gave colorless prism crystals of mp 55°–56° C.

Elementary analysis for $C_{12}H_{13}NO_2$: Calc. (%): C, 70.92; H, 6.45; N, 6.89; Found (%): C, 70.65; H, 6.35; N, 6.67.

Example 41

To a solution of 3-[4-(4-chlorophenyl)-2-oxazolyl]propanol (1.0 g) in dichloromethane (10 ml) were added dimethylsulfoxide (0.6 ml) and phosphoric anhydride (1.1 g) in that order. After stirring for 10 minutes at room temperature, the resultant was cooled to 0° C., to which triethylamine (2 ml) was added. The mixture was stirred for 40 minutes at room temperature, poured into 2N-HCl and extracted with dichloromethane. The dichloromethane layer was washed with water, dried over MgSO4, and distilled to remove the solvent. The oily residue was subjected to a silica gel column chromatography. Crystals of 3-[4-(4-chlorophenyl)-2-oxazolyl]propanal (0.698 g, 70%) were obtained from the fraction eluted with ethyl acetate-hexane (1:3, V/V). Recrystallization from hexane gave colorless prism crystals of mp 41°–42° C.

Elementary analysis for $C_{12}H_{10}NO_2Cl$: Calc. (%): C, 61.16; H, 4.28; N, 5.94; Found (%): C, 61.10; H, 4.21; N, 5.91.

Example 42

To a solution 3-[4-(4-chlorophenyl)-2-oxazolyl] propanol (0.5 g) in pyridine (5 ml) was added acetic anhydride (1.0 ml), followed by stirring for 30 minutes at 50° to 60° C. The reaction mixture was poured into water. The precipitated crystals were collected by filtration to obtain 3-[4-(4-chlorophenyl)-2-oxazolyl]propyl acetate (0.535 g, 91%). Recrystallization from ether-hexane gave colorless prism crystals of mp 37°–37.5° C.

Elementary analysis for $C_{14}H_{14}NO_3Cl$; Calc. (%): C, 60.11; H, 5.04; N, 5.01; Found (%): C, 60.12; H, 5.06; N, 5.18.

Example 43

To a solution of 3-[4-(4-chlorophenyl)-2-oxazolyl] propanol (0.5 g) in pyridine (2 ml) was added benzoyl chloride (0.29 ml), followed by stirring for an hour at room temperature. The reaction mixture was poured into water and extracted with ethyl acetate. The ethyl acetate layer was washed successively with an aqueous sodium hydrogen carbonate solution 2N-HCl and water, dried over MgSO4, and distilled to remove the solvent. The precipitated crystals were collected by filtration to give 3-[4-(4-chlorophenyl)-2-oxazolyl]propyl benzoate (0.687 g, 96%). Recrystallization from ether-hexane gave colorless prism crystals of mp 47°–47.5° C.

Elementary analysis for $C_{14}H_{14}NO_3Cl$: Calc. (%): C, 66.77; H, 4.72; N, 4.10; Found (%): C, 66.72; H, 4.70; N, 3.98.

Example 44

To a solution of 3-[4-(4-chlorophenyl)-2-oxazolyl] propanol (0.6 g) in DMF (10 ml) were added 60% (W/W) sodium hydride in oil (0.12 g) and benzyl bromide (0.3 ml), followed by stirring for 3 hours at room temperature. After additional stirring for an hour at 30° C., the reaction mixture was poured into water and then extracted with ether. The ether layer was washed with water, dried over MgSO4, and distilled to remove the solvent. The oily residue was subjected to a silica gel column chromatography. Oily 3-[4-(4-chlorophenyl)-2-oxazolyl]propyl benzyl ether (0.512 g, 62%) was obtained from the fraction eluted with ether-hexane (1:4, V/V).

NMR (δppm, CDCl3): 1.9–2.3(2H, m), 2.93(2H, t, J=7.5 Hz), 3.57(2H, t, J=6.5 Hz), 4.52(2H, s), 7.35(5H, s), 7.37(2H, d, J=9 Hz), 7.67(2H, d, J=9 Hz), 7.80(1H, s).

Elementary analysis for $C_{19}H_{18}NO_2Cl$: Calc. (%): C, 69.62; H, 5.53; N, 4.27; Found (%): C, 69.84; H, 5.48; N, 4.03.

Example 45

3-[4-(4-chlorophenyl)-2-oxazolyl]propanol (5.21 g) and triethylamine (4 ml) were dissolved in dichloromethane (50 ml), to which methanesufonyl chloride (2.2 ml) was dropwise added under ice-cooling and stirred for 2 hours at the same temperature. The reaction mixture was poured into water and then extracted with dichloromethane. The dichloromethane layer was washed with water, dried over MgSO₄ and distilled to remove the solvent. The oily residue was dissolved in acetone (100 ml), to which sodium iodide (6.6 g) was added and refluxed for 2 hours. The solvent was distilled off. The residue was poured into water and extracted with ether. The ether layer was washed with an aqueous Na$_2$SO$_3$ solution and then water, and dried over MgSO$_4$. The solvent was distilled off to obtain 4-(4-chlorophenyl)-2-(3-iodopropyl)oxazole (6.6 g, 87%). Recrystallization from ether-hexane gave colorless prism crystals of mp 49°–50° C.

Elementary analysis for $C_{12}H_{11}NOClI$: Calc. (%): C, 41.47; H, 3.19; N, 4.03; Found (%): C, 41.46; H, 3.06; N, 4.03.

Example 46

A mixture of 4-(4-chlorophenyl)-2-(3-iodopropyl)oxazole (0.5 g), guaiacol (0.19 ml), potassium carbonate (0.24 g) and N,N-dimethylformamide (5 ml) was stirred for 30 minutes at 60° to 65° C. and poured into water. The precipitated crystals were collected by filtration to obtain 4-(4-chlorophenyl)-2-[3-(2-methoxyphenoxy)propyl]oxazole (0.445 g, 90%). Recrystallization from ether-hexane gave colorless prism crystals of mp 94°–95° C.

Elementary analysis for $C_{19}H_{18}NO_3Cl$: Calc. (%): C, 66.38; H, 5.28; N, 4.07; Found (%): C, 66.01; H, 5.20; N, 3.96.

Examples 47–51

By the method of Example 46, the compounds listed in Table 7 were obtained.

Examples 52–58

By the method of Example 1, the compounds listed in Table 2 were obtained.

Examples 59–65

By the method of Example 12, the compounds listed in Table 3 were obtained.

Examples 66–69

By the method of Example 24, the compounds listed in Table 4 were obtained.

Examples 70 and 72

By the method of Example 37, the compounds listed in Table 6 were obtained.

Examples 71 and 73

By the method of Example 40, the compounds listed in Table 6 were obtained.

Examples 74–76

By the method of Example 46, the compounds listed in Table 7 were obtained.

Test example

In the following test examples, the results of the pharmacological test which show the usefulness of the compounds of the present invention are described.

Test Example 1: Blood sugar lowering activity

Method:

Blood glucose lowering activity of the compounds of the present invention in fasted test subjects was examined using male KKA$^y$ mice with hereditary obese diabetes (ten-week old, one group consisting of five mice). A suspension of the test compound in a 5% gum arabic solution (30 mg/kg) was forcedly and orally administered to KKA$^y$ mice which had been fasted for 20 hours beforehand. Sixty minutes and 120 minutes later, blood was drawn from the orbital sinus of each mouse and the blood glucose value was measured by the glucose oxidase method. The intensity of the activity of the test compound was indicated as a lowering ratio (%) of the blood glucose value of the group of mice administered a test compound relative to that of the control group of mice not administered it.

Results: The test results are shown in Table 1

TABLE 1

| Compound (Example No.) | Blood glucose lowering ratio (%) | |
|---|---|---|
| | After 60 minutes | After 120 minutes |
| 6 | 34 | 36 |
| 11 | 39 | 42 |
| 14 | 31 | 23 |
| 15 | 32 | 35 |
| 21 | 30 | 33 |
| 23 | 32 | 31 |
| 24 | 21 | 21 |
| 34 | 22 | 24 |
| 35 | 25 | 18 |
| 37 | 33 | 35 |
| 40 | 20 | 24 |
| 41 | 26 | 21 |
| 42 | 30 | 21 |
| 43 | 24 | 21 |
| 46 | 24 | 29 |

It is apparent from the results in Table 1 that the compounds of the present invention exhibit an excellent blood glucose lowering activity.

Test example 2: Glucose tolerance improving activity

Method:

Glucose tolerance activity of the compounds was tested using male GK rats with spontaneously occurring diabetes and glucose intolerance (9-week ole, one group consisting of five rats). The rats were fasted for 20 hours and received an oral administration of 30 mg/kg of the test compound (Compound No. 37 suspended in 5% gum arabic solution). Sixty minutes later, 40% glucose solution (2g/kg) was orally administered. Immediately before and, 15, 30, 60 and 120 minutes after the adminitration of glucose, blood was drawn from the orbital sinus of each rat. The values of blood glucose and plasma insulin were measured.

Results: The blood glucose reaction in the rat group which received the test compound was significantly lower in comparison with that in the control rat group. Namely, the blood glucose values of the test rat group measured immediately before and, 15, 30, 60 and 120 minutes after the glucose administration lowered to 69, 79, 71, 56 and 39% of those of the control rat group, respectively. On the other hand, plasma insulin secreting response of the test group was higher in comparison with that of the control group. Namely, the plasma insulin values measured immediately before and, 15, 30, 60 and 120 minutes after the glucose administration increased to 128, 210 179, 131 and 104% of those of the control group, respectively.

It is apparent from the above results that the compound of the present invention exhibits a glucose tolerance improving property.

Preparation Example 1

Tablet

Components a tablet

| | | |
|---|---|---|
| (1) Compound (as obtained by Example 41) | 50 | mg |
| (2) Cornstarch | 30 | mg |
| (3) Lactose | 113.4 | mg |
| (4) Hydroxypropyl cellulose | 6 | mg |
| (5) Water | (0.03 | ml) |
| (6) Magnesium stearate | 0.6 | mg |
| Total | 200 | mg |

The components (1), (2), (3) and (4) were mixed. After adding water, the mixture was kneaded, dried under vacuum for 16 hours at 40° C. and grounded in a mortar. The resultant was sieved through a 16-mesh sieve to obtain granules. The component (6) was added to the granules and mixed. The resulting mixture was made into tablets of 200 mg per tablet, using a rotary-type tablet machine (Kikusui Seisakusho in Japan).

Preparation Example 2

| | | |
|---|---|---|
| (1) Compound (as obtained by Example 37) | 50 | mg |
| (2) Cornstarch | 30 | mg |
| (3) Lactose | 113.4 | mg |
| (4) Hydroxypropyl cellulose | 6 | mg |
| (5) Water | (0.03 | ml) |
| (6) Magnesium stearate | 0.6 | mg |
| (7) Cellulose acetate phthalate | 10 | mg |
| (8) Acetone | (0.2 | ml) |
| Total | 210 | mg |

From the components (1), (2), (3), (4), (5) and (6), tablets were prepared by the same method as in Preparation Example 1. These tablets were film-coated by use of a solution of the component (7) in acetone in a half coater (Freunt Co., Ltd) to give entric tablets of 210 mg per tablet.

Preparation Example 3

Components of a capsule

| | | |
|---|---|---|
| (1) Compound (as obtained by Example 24) | 30 | mg |
| (2) Cornstarch | 40 | mg |
| (3) Lactose | 74 | mg |
| (4) Hydroxypropyl cellulose | 6 | mg |
| (5) Water | 0.02 | mg |
| Total | 150 | mg |

The components (1), (2), (3) and (4) were mixed, and water was added. The mixture was kneaded, dried under vacuum for 16 hours at 40° C. and grounded in a mortar. The resultant was sieved through a 16-mesh sieve to obtain granules. The granules were packed in No. 3 gelatin capsules with a capsule packing machine (Zanasi Italy) to obtain capsules.

Preparation Example 4

| | | |
|---|---|---|
| (1) Compound (as obtained by Example 14) | 5 | mg |
| (2) Sodium salicylate | 50 | mg |
| (3) Sodium chloride | 180 | mg |
| (4) Sodium metabisulfite | 20 | mg |
| (5) Methylparaben | 36 | mg |
| (6) Propylparaben | 4 | mg |
| (7) Distilled water for injection | (2 | ml) |
| Total | 295 | mg |

The components (2), (3), (4), (5) and (6) were dissolved in about one half of the above mentioned volume of distilled water under stirring at 80° C. The solution thus obtained was cooled to 40° C., and the compound of the present invention was dissolved. The remaining distilled water was added to the solution so that a final volume could be obtained. The resultant was sterilized through an appropriate filter paper, to obtain the injection.

From the results shown by the above Test Examples, the compounds (I) or (I') of the present invention have blood glucose lowering activity and glucose tolerance improving activity in mammals (for example, mouse, rat, rabbit, dog, cat, bovine, swine, human, etc.) and in addition have low toxicity.

Accordingly, the compounds (I) and (I') of the present invention or salts thereof can be used for a remedy for diabetes of mammals.

TABLE 2

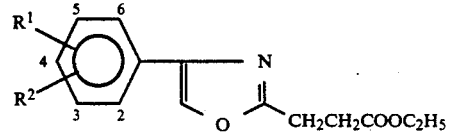

| No. of Example | $R^1$, $R^2$ | Yield (%) | MP (°C.) | Solvent for recrtstallization |
|---|---|---|---|---|
| 2 | H, H | 60 | Oil[note 1)] | |
| 3 | 3-Cl, 4-Cl | 59 | 65–66 | Ether-hexane |
| 4 | 3-F, 4-F | 67 | Oil[note 2)] | — |
| 5 | 4-CN, H | 53 | 66–67 | Ether-hexane |
| 6 | 4-CF$^3$, H | 64 | 62–63 | Ether-hexane |
| 7 | 4-NO$_2$, H | 60 | 97–98 | Acetone-hexane |
| 8 | 4-OCHF$_2$, H | 59 | 60–61 | Ether-hexane |
| 9 | 4-OCF$_3$, H | 62 | 36–37 | Hexane |
| 10 | 4-CH$_3$, H | 63 | Oil[note 3)] | — |
| 52 | 3-NO$_2$, H | 56 | 76–77 | Ether-hexane |
| 53 | 2-Cl, 4-Cl | 70 | Oil[note 4)] | — |
| 54 | 4-C$_2$H$_5$, H | 58 | Oil[note 5)] | — |
| 55 | 3-CF$_3$, H | 36 | 60–61 | Ether-hexane |
| 56 | 2-CF$_3$, H | 34 | Oil[note 6)] | — |
| 57 | 3-NO$_2$, 4-Cl | 72 | 65–66 | Ether-hexane |
| 58 | 2-Cl, 4-NO$_2$ | 48 | 71–72 | Ether-hexane |

Note 1)NMR(δ ppm, CDCl$_3$): 1.25(3H, t, J=7.5Hz), 2.7–3.3(4H, m), 4.17(2H, q, J=7.5Hz), 7.2–7.55(3H, m), 7.6–7.8(2H, m), 7.81(1H, s).
Note 2)NMR(δ ppm, CDCl$_3$): 1.25(3H, t, J=7.5Hz), 2.7~3.3(4H, m), 4.17(2H, q, J=7.5Hz), 6.95~7.3(3H, m), 7.77(1H, s).
Note 3)NMR(δ ppm, CDCl$_3$): 1.24(3H, t, J=7.5Hz), 2.34(3H, s), 2.7–3.3(4H, m), 4.16(2H, q, J=7.5Hz), 7.17(2H, d, J=8.5Hz), 7.57(2H, d, J=8.5Hz), 7.75(1H, s).
Note 4)NMR(δ ppm, CDCl$_3$): 1.24(3H, t, J=7.0Hz), 2.7–3.3(4H, m), 4.15(2H, q, J=7.0Hz), 7.2–7.5(2H, m), 8.05(1H, d, J=9.0Hz), 8.23(1H, s).
Note 5)NMR(δ ppm, CDCl$_3$): 1.24(6H, m), 2.5–3.3(6H, m), 4.15(2H, q, J=7.0Hz), 7.22(2H, d, J=9.0Hz), 7.62(2H, d, J=9.0Hz), 7.77(1H, s).
Note 6)NMR(δ ppm, CDCl$_3$): 1.26(3H, t, J=7.0Hz), 2.7–3.3(4H, m), 4.18(2H, q, J=7.0Hz), 7.3–8.1(5H, m).

TABLE 3

| No. of Example | $R^1$, $R^2$ | Yield (%) | MP (°C.) | Solvent for recrystallization |
|---|---|---|---|---|
| 13 | H, H | 67 | 119–120 | Ether-hexane |
| 14 | 4-Cl, H | 92 | 137–138 | Acetone-hexane |
| 15 | 3-Cl, 4-Cl | 83 | 126–127 | Acetone-hexane |
| 16 | 3-F, 4-F | 94 | 119–120 | Ether-hexane |
| 17 | 4-CN, H | 82 | 167–168 | Acetone-hexane |
| 18 | 4-NO$_2$, H | 87 | 180–181 | Acetone-hexane |
| 19 | 4-CF$_3$, H | 78 | 151–152 | Acetone-hexane |
| 20 | 4-OCHF$_2$, H | 73 | 108–109 | Ether-hexane |
| 21 | 4-OCF$_3$, H | 78 | 118–119 | Ether-hexane |
| 22 | 4-CH$_3$, H | 79 | 128–129 | Acetone-hexane |

TABLE 3-continued

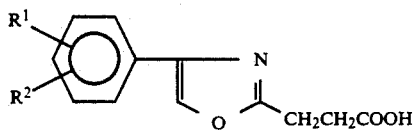

| No. of Example | R¹, R² | Yield (%) | MP (°C.) | Solvent for recrystallization |
|---|---|---|---|---|
| 59 | 3-NO₂, H | 89 | 152-153 | Acetone-hexane |
| 60 | 2-Cl, 4-Cl | 85 | 137-138 | Acetone-hexane |
| 61 | 4-C₂H₅, H | 80 | 123-124 | Ether-hexane |
| 62 | 3-CF₃, H | 93 | 93-94 | Ether-hexane |
| 63 | 2-CF₃, H | 91 | 55-56 | Ether-hexane |
| 64 | 3-NO₂, 4-Cl | 85 | 186-187 | Acetone-hexane |
| 65 | 2-Cl, 4-NO₂ | 92 | 156-157 | Acetone-hexane |

TABLE 4

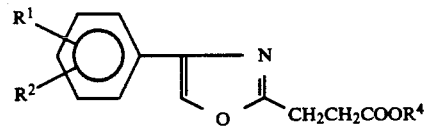

| No. of Example | R¹, R² | R⁴ | Yield (%) | MP (°C.) | Solvent for recrystallization |
|---|---|---|---|---|---|
| 25 | H, 4-Cl | 1-naphthyl-CH₂— | 92 | 69-70 | Ether-hexane |
| 26 | H, 4-Cl | 2,6-dichlorobenzyl | 89 | 62-63 | Ether-hexane |
| 27 | H, 4-Cl | cycloheptyl | 90 | 37-38 | Ether-hexane |
| 66 | H, 4-Cl | —CH₂CH₂N(CH₃)₂·HCl | 85 | 160-161 | Dechloromethaneethanol |
| 67 | H, 4-Cl | —CH₂—C₆H₄—Cl (4-Cl) | 89 | 77-78 | Ether-hexane |
| 68 | H, 4-Cl | —CH(Me)—C₆H₅ | 76 | 52-53 | Ether-hexane |
| 69 | H, 4-Cl | —CH₂—C₆H₄—CH₃ (2-Me) | 73 | 47-48 | Ether-hexane |

TABLE 5

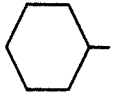

| No. of Example | $R^1, R^2$ | $R^4$ | Yield (%) | MP (°C.) | Solvent for recrystallization |
|---|---|---|---|---|---|
| 29 | H, 4-Cl | cyclohexyl | 54 | 38-39 | Hexane |
| 30 | H, 4-Cl | (Me)C=CH-CH₂CH₂-C(Me)=CH-CH₂— | 73 | Oil[1] | — |
| 31 | H, 4-Cl | 2,4-dimethoxybenzyl | 61 | 72-73 | Dichloromethaneethanol |

[1]NMR(δ ppm, CDCl₃): 1.59(3H, s), 1.68(6H, s), 1.95-2.2(4H, m), 2.7-3.3(4H, m), 4.64(2H, d, J=7Hz), 5.08(1H, bs), 5.34(1H, bt, J=7Hz), 7.34(2H, d, J=9Hz), 7.64(2H, d, J=9Hz), 7.80(1H, s).

TABLE 6

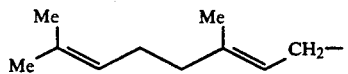

| No. of Example | $R^1, R^2$ | Yield (%) | MP (°C.) | Solvent for recrystallization |
|---|---|---|---|---|
| 38 | H, 4-CH₃ | 73 | 41-42 | Ether-hexane |
| 39 | H, 4-CF₃ | 82 | 61-61.5 | Ether-hexane |
| 70 | H, 4-NO₂ | 38 | 86-87 | Dichloromethnaneethanol |

TABLE 6-continued

| No. of Example | $R^1, R^2$ | Yield (%) | MP (°C.) | Solvent for recrystallization |
|---|---|---|---|---|
| 71 | H, 4-OCHF₂ | 98 | 56-57 | Ether-hexane |
| 72 | H, 4-OCF₃ | 78 | 77-78 | Ether-hexane |
| 73 | H, 4-CN | 65 | 101-102 | Dichloromethaneethanol |

TABLE 7

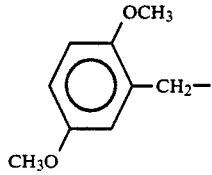

| No. of Example | $R^1, R^2$ | $R_3$ | Yield (%) | MP (°C.) | Solvent for recrystallization |
|---|---|---|---|---|---|
| 47 | H, 4-Cl | phenyl | 78 | 99-100 | Ether-hexane |
| 48 | H, 4-Cl | 2-ethoxyphenyl (C₂H₅O-) | 71 | 56-57 | Ether-hexane |

TABLE 7-continued

Structure: phenyl ring with R¹, R² substituents connected to a vinyl-oxazoline containing N, O and CH₂CH₂CH₂OR³ chain.

| No. of Example | R¹, R² | R₃ | Yield (%) | MP (°C.) | Solvent for recrystallization |
|---|---|---|---|---|---|
| 49 | H, 4-Cl | 2,3-dimethoxyphenyl (CH₃O, CH₃O) | 61 | 66–67 | Ether-hexane |
| 50 | H, 4-Cl | 2-acetylphenyl (CH₃CO) | 82 | 79–80 | Ether-hexane |
| 51 | H, 4-Cl | 2-methoxycarbonylphenyl (CH₃OOC) | 85 | Oil[note 1] | — |
| 74 | H, 4-Cl | 2,4-dimethoxyphenyl (OCH₃, OCH₃) | 71 | 68–69 | Ether-hexane |
| 75 | H, 4-Cl | 2-hydroxyphenyl (HO) | 54 | 118–119 | Dechloromethane-ethanol |
| 76 | H, 4-Cl | 2-chlorophenyl (Cl) | 78 | 57–58 | Hexane |

Note 1) NMR(δ ppm CDCl₃): 2.15–2.5(2H, m)

The present applicants have learned that as the invention of Takashi Sohda, Iwao Yamazaki and Yu Momose, a further use for the compounds of the present invention is for the therapy of metabolic bone disease including osteoporosis.

As an example, to test the bone-reduction inhibitory action of 3-[4-(4-chlorophenyl)-2-oxazolyl]propanol (compound A), an oophorectomy-operated rat which is generally used as a typical experimental animal for postmenopausal osteoporosis was used. Oophorectomy was operated on a female Sprague-Dawley rat 10 weeks old. From the next day after the operation, 20 mg/kg of a specimen of the compound A (suspended in aqueous solution of 1% of hydroxypropyl cellulose) was given to the rat 3 times a week for 3 weeks by forced oral administration. The next day after the final administration, the right femur of the rat was extirpated and cut to give ⅓ of the femur from the distal end. This portion of the femur was dried at 110° C. for 3 hours, then weighed, and further incinerated at 500° C. for 3 hours and subsequently at 800° C. for 2 hours, then weighed.

The result of the test is shown in the following table.

TABLE 8

| Group | No. of tested rats | Dry weight(mg) | Ashes (mg) |
|---|---|---|---|
| Sham operation Control | 6 | 138.2 ± 3.4* | 89.0 ± 2.3* |
| Oophorectomy Control | 5 | 120.0 ± 3.2 | 74.9 ± 2.2 |
| Compound A Treatment group | 5 | 132.9 ± 2.9* | 83.7 ± 1.7* |

*$p < 0.05$ (compared with oophorectomized controls)

As can be obviously understood from the table, both the dried and incinerated states of the femur decreased in weight due to the oophorectomy, however, the decrease was significantly inhibited by the compound A.

The details of this utility are more fully described in the Japanese patent application no. 023033-1990 of Takeda Chemical Industries, Ltd., in the name of Takashi Sohda, Iwao Yamazaki and Yu Momose entitled "Oxazole compounds and their use", filed on Feb. 1, 1990. The entire disclosure of the aforementioned Japanese patent application is hereby incorporated herein by reference.

This application discloses that the compounds disclosed in that application and their salts possess bone-reduction inhibitory action as well as bone-increase action in mammals (e.g., mouse, rat, rabbit, dog, cat, cow, pig and human being) and their toxicity is very low. Thus, they can be used as an a therapeutic agent for metabolic bone disease including osteroporosisof mammals (e.g., mouse, rat, rabbit, dog, cat, cow, pig and human being).

The compounds of the invention can be administered to human being through any of oral or parental route.

Compositions for oral administration may be solid or liquid forms, specially tablets (including sugar coated tablets and film coated tablets), pills, granules, powders, capsules (including soft capsules), syrups, emulsions and suspensions. Such compositions will contain conventional carriers or excipients and can be prepared by known methods. Examples of carriers or excipients for tablets are lactose, starch, sucrose and magnesium stearate.

Compositions for parental administration are e.g., injections and suppositories, the former of which includes subcutaneous, intracutaneous, intramuscular or like injections. Such injections can be prepared by suspending or emulsifying the compound (I'') or (I'''), or salt thereof in or with sterile aqueous or oily liquids which are usually employed in injections, in accordance with the methods known in the art. Examples of the aqueous liquids for injections are physiological saline and isotonic solution, which may be used together with a suitable suspending agent such as sodium carboxy methylcellulose or a nonionic surfactant upon circumstances. Examples of the oily liquids are sesame oil and soybean oil, which may be used together with a solubilizing agent such as benzyl benzoate or benzyl alcohol. The injections thus prepared are usually put into ampules.

The oral dosage of the compounds (I'') or (I'''), or salts thereof when used as therapeutic agent for metabolic bone desease is 1 to 500 mg/day/adult, preferably 10 to 150 mg.

The invention is further illustrated by examples, test examples and preparation examples, by which no limitation shall be not given.

Test Example 1

Bone-reduction inhibitory action

The bone-reduction inhibitory action was tested by using an ovariectomy-operated rat which is generally used as a typical experimental animal for postmenopausal osteroporosis. Ovariectomy was operated on a female Sprague-Dawley rat 10 week old. From the next day of the operation, 20 mg/kg of a specimen of the compound obtained in Example 81 (suspended in aqueous solution of 1% of hydroxypropyl cellulose) was given to the rat 3 times a week for 3 weeks by forced oral administration. The next day of the final administration, the right femur of the rat was extirpated and cut to give ⅓ of the femur from the distal end. This portion of the femur was dried at 110° C. for 3 hours, then weighed, and further incinerated at 500° C. for 3 hours and subsequently at 800° C. for 2 hours, then weighed.

The result of the test is shown in Table 1'.

TABLE 1'

| Group | No. of tested rats | Dry weight(mg) | Ashes (mg) |
|---|---|---|---|
| Sham operation (Control) | 6 | 138.2 ± 3.4* | 89.0 ± 2.3* |
| Ovariectomy (Control) | 5 | 120.0 ± 3.2 | 74.9 ± 2.2 |
| (Compound No. 81 Treatment group | 5 | 132.9 ± 2.9* | 83.7 ± 1.7* |

*$p < 0.05$ (significant difference relative to the average ovariectomy contols) (t-assay)

As can be obviously understood from the Table 1', both the dried and incinerated states of the femur decreased in weight due to the ovariectomy, however, the decrease was significantly inhibited by the compound of the present invention.

Test Example 2'

Bone-increase action 20 mg/kg/day or 100 mg/kg/day of a specimen of the compound obtained in Example 81' (suspended in aqueous solution of 1% of hydroxypropyl cellulose) was given to a normal male Sprague-Dawley rat 5 week old, 3 times a week by forced oral administration. The next day of the final administration, the right femur of the rat was extirpated and cut to give ⅓ of the femur from the distal end. This portion of the femur was treated by the same manner as in Test Example 1', weighing both the dried and incinerated states of the femur.

The result of the test is shown in Table 2'.

TABLE 2'

| Group | No. of tested rats | Dry weight(mg) | Ashes (mg) |
|---|---|---|---|
| Normal (Control) | 6 | 111.1 ± 3.5 | 64.3 ± 2.0 |
| Compound No. 81 Treatment group (20 mg/kg/day) | 6 | 117.0 ± 3.7 | 68.5 ± 2.1 |
| Compound No. 81 Treatment group (100 mg/kg/day) | 6 | 120.2 ± 1.5* | 69.4 ± 1.1* |

*$p < 0.05$ (significant difference relative to the average normal contols) (t-assay)

As can be obviously understood from the Table 2', both the dried and incinerated states of the femur increased in weight due to the compound of the present invention in an amount of 20 mg/Kg/day, and further increased significantly by the compound of the present invention in an amount of 100 mg/Kg/day.

Example 1'

A mixture of 3,5-ditrifluoromethylphenacyl bromide (3.1 g) and ethyl succinamate monoamide (5.4 g) was heated for 2 hours at 130° C. The reaction mixture was poured into water. The precipitated crystals were collected by filtration to obtain ethyl 4-(3,5-ditrifluoromethylphenyl)-2-oxazolepropionate (1.7 g, 47%). Recrystallization from hexane gave colorless prism crystals of mp 70°–71° C.

Elementary analysis for $C_{16}H_{13}NO_3F_6$ Calcd. (%): C, 50.40; H, 3.44; N, 3.67; Found (%): C, 50.62; H, 3.40; N, 3.70.

Examples 2'-18'

By the method of Example 1, the compounds listed in Table 3' were obtained.

Example 19'

To a solution of 4-chloro-α-hydroxyacetophenone (4.84 g) in pyridine (50 ml) was added ethyl succinyl chloride (4.8 ml) at room temperature, followed by stirring for 2 hours. The reaction mixture was poured into water and extracted with ethyl acetate. The ethyl acetate layer was washed successively with 6N-HCl and water, and dried over $MgSO_4$. After distilling off the solvent, the oily residue was subjected to a silica gel column chromatography. Crystals (7.85 g, 93%) of 2-(4-chlorophenyl)-2-oxoethyl ethyl succinate were obtained from the fraction eluted with ethyl acetate-hexane (1:2, V/V). Recrystallization from ether-hexane gave colorless needle crystals of mp 50°-51° C.

Elementary analysis for $C_{14}H_{15}O_5Cl$: Calcd.: C, 56.29; H, 5.06; Found: C, 56.55; H, 5.08.

A mixture of 2-(4-chlorophenyl)-2-oxoethyl ethyl succinate (7.6 g), ammonium acetate (9.8 g) and acetic acid (80 ml) was stirred for an hour at 110° C. and refluxed for 2 hours. The solvent was distilled off. The residue was diluted with water, made basic by addition of aqueous sodium hydrogen carbonate solution and then extracted with ethyl acetate. The ethyl acetate layer was washed with water, and dried over $MgSO_4$. After removal of the solvent, the oily residue was subjected to a silica gel column chromatography. Crystals of ethyl 4-(4-chlorophenyl)-2-oxazolepropionate (2.23 g, 31%) were obtained from the fraction eluted with ethyl acetate-hexane (1:3, V/V). Recrystallization from ethyl acetate-hexane gave colorless plate crystals of mp 65°-66° C.

Elementary analysis for $C_{14}H_{14}NO_3Cl$: Calcd. (%): C, 60.11; H, 5.04; N, 5.01; Found (%): C, 59.96; H, 5.07; N, 5.01.

Examples 20' to 28'

By the same manner as in Example 19', compounds listed in Table 4' were obtained.

Example 29'

A mixture of 1-amino-1-(4-chlorophenyl)-2-propanone hydrochloride (1.0 g), ethyl malonyl chloride (0.75 g) and benzene (20 ml) was refluxed for 2.5 hours. After distilling off the solvent, water was added to the residue. The mixture was made neutral by the addition of saturated aqueous sodium hydrogen carbonate solution. The resultant solution was extracted with ethyl acetate. The ethyl acetate layer was washed with water, dried ($MgSO_4$), and distilled to remove the solvent, thereby giving crystals (1.29 g, 95%) of ethyl N-[1-(4-chlorophenyl)-2-oxopropyl] malonate monoamide as oil.

NMR (δppm, $CDCl_3$): 1.27(3H, t, J=7.5 Hz), 2.11(3H, s), 3.20(2H, s), 4.20(2H, q, J=7.5 Hz), 5.5 (1H, d, J=6.0 Hz), 7.15-7.6(4H, m), 8.29(1H, broad d).

Thus obtained compound (1.29 g) was dissolved in toluene (10 ml), to which phosphorus oxychloride (0.39 mg) was added. The mixture was refluxed for 40 minutes. The solvent was distilled off under the reduced pressure. The residue was diluted with water, made neutral by addition of saturated aqueous sodium hydrogen carbonate solution and then extracted with ethyl ether. The ether layer was washed with water, dried over $MgSO_4$ and distilled to remove the solvent. The oily residue was subjected to a silica gel column chromatography. Oily ethyl 4-(4-chlorophenyl)-5-methyl-2-oxazoleacetate (0.8 g, 66%) was obtained from the fraction eluted with ethyl acetate-hexane (1:5, V/V).

NMR (δppm, $CDCl_3$): 1.27(3H, t, J=7.5 Hz), 2.49(3H, s), 3.81(2H, s), 4.22(2H, q, J=7.5 Hz), 7.35 (2H, d, J=9.0 Hz), 7.57 (2H, d, J=9.0 Hz).

Examples 30'-32'

By the same manner as in Example 29', the compounds listed in Table 5' were obtained.

Example 33'

Ethyl 4-(3,5-ditrifluoromethylphenyl)-2-oxazolepropionate (1.6 g) was dissolved in methanol (20 ml), to which 10% NaOH (10 ml) was added. After stirring for 10 minutes at room temperature, the mixture was poured into water. The resultant was extracted with ethyl ether. The aqueous layer was made acidic with 2N-HCl and the precipitated crystals of 4-(3,5-ditrifluoromethylphenyl)-2-oxazolepropionic acid (1.3 g, 87%) were collected by filtration. Recrytallization from ether-hexane gave colorless prism crystals of mp 130°-131° C.

Elementary analysis for $C_{14}H_9NO_3F_6$: Calc. (%): C, 47.61; H, 2.57; N, 3.97: Found (%): C, 47.38; H, 2.53; N, 3.97.

Examples 34'-62'

By the method of Example 33', the compounds listed in Table 6' were obtained.

Example 63'

To a mixture of 4-(4-chlorophenyl)-2-oxazolepropionic acid (0.5 g) and isopropanol (30 ml) was added conc. sulfuric acid (0.3 ml), and the resultant was refluxed for 5 hours. The reaction mixture was poured into water and extracted with ether. The ether layer was washed succesively with a saturated sodium hydrogen carbonate aqueous solution and water, and dried over $MgSO_4$. The ether was distilled off to give crystals of isopropyl 4-(4-chlorophenyl)-2-oxazolepropionate (530 mg, 91%). Recrystallization from hexane gave colorless prism crystals of mp 30°-31° C.

Elementary analysis for $C_{15}H_{16}NO_3Cl$: Calc. (%): C, 61.33; H, 5.49; N, 4.77: Found (%): C, 61.18; H, 5.49; N, 4.77.

Example 64'

A mixture of 4-(4-chlorophenyl)-2-oxazoleproprionic acid (0.5 g), benzyl bromide (0.25 ml), potassium carbonate (0.33 g) and dimethylformamide (DMF) (10 ml) was stirred for 3 hours at room temperature. The reaction mixture was poured into water to obtain crystals of benzyl 4-(4-chlorophenyl)-2-oxazolepropionate (0.664 g, 98%). Recrystallization from ether-hexane gave colorless prism crystals of mp 66°-67° C.

Elementary analysis for $C_{19}H_{16}NO_3Cl$: Calc. (%): C, 66.77; H, 4.72; N, 4.10; Found (%): C, 66.91; H, 4,69; N, 4.02.

Examples 65'-72'

By the method of Example 64', the compounds listed in Table 7' were obtained.

Example 73'

To a solution of 4-(4-chlorophenyl)-2-oxazolepropionic acid (0.7 g) in tetrahydrofuran (THF) (20 ml), were added oxalyl chloride (0.27 ml) and DMF (one drop) at 0° C. After stirring for 2 hours at room temperature, the solvent was distilled off. The oily residue was dissolved THF (10 ml), to which 3,4,5-trimethoxybenzyl alcohol (1.1 g) and triethylamine (1.2 ml) were added in that order. After stirring for 4 hours at room temperature, the mixture was poured into water and then extracted with ether. The ether layer was washed with water and dried over $MgSO_4$. After distilling off the solvent, the oily residue was subjected to a silica gel column chromatography. Crystals of 3,4,5-trimethoxybenzyl 4-(4-chlorophenyl)-2-oxazolepropionate (0.743 g, 62%) were obtained from the fraction eluted with ethyl acetate-hexane. Recrystallization from dichloromethane-hexane gave colorless prism crystals of mp 86°–87° C.

Elementary analysis for $C_{22}H_{22}NO_6Cl$: Calc. (%): C, 61.19; H, 5.13; N, 3.24; Found (%): C, 61.29; H, 5.12; N, 3.33.

Examples 74'–76'

By the method of Example 73, the compounds listed in Table 8' were obtained.

Example 77'

To a solution of 4-(4-chlorophenyl)-2-oxazolepropionic acid (0.5 g) in dichloromethane (20 ml) was added diphenyldiazomethane (0.425 g). After stirring for 4 hours at room temperature, acetic acid (0.5 ml) was added to the mixture. The reaction mixture was washed with a saturated sodium hydrogen carbonate aqueous solution and water, and then dried over $MgSO_4$. The solvent was distilled off and then the oily residue was subjected to a silica gel column chromatography. Crystals of diphenylmethyl 4-(4-chlorophenyl)-2-oxazolepropionate (0.759 g, 91%) were obtained from the fraction eluted with ether-hexane (1:3, V/V). Recrystallization from ether-hexane gave colorless prism crystals of mp 94°–95° C.

Elementary analysis for $C_{25}H_{20}NO_3Cl$: Calc. (%): C, 71.85; H, 4.82; N, 3.35; Found (%): C, 71.83; H, 4.79; N, 3.38.

Example 78'

To a solution of 4-(4-chlorophenyl)-2-oxazolepropionic acid (0.5 g) in acetonitrile (20 ml) were added 2-phenyl-2-propanol (0.325 g), dicyclohexylcarbodiimide (0.49 g) and 4-dimethylaminopyridine (0.025 g), followed by stirring for 65 hours at room temperature. 2-Phenyl-2-propanol (0.325 g), dicyclohexylcarbodiimide (0.49 g) and 4-dimethylaminopyridine (0.025 g) were further added to the reaction mixture, followed by stirring for 2 hours at 50° C. The reaction mixture was filtered to remove an insoluble substance, and the filtrate was then concentrated. The oily residue was subjected to a silica gel column chromatography. Crystals of 1-methyl-1-phenylethyl 4-(4-chlorophenyl)-2-oxazdepropionate (0.297 g, 38%) were obtained from the fraction eluted with ethyl acetate-hexane (1:4, V/V). Recrystallization from hexane gave colorless prism crystals of mp 94°–95° C.

Elementary analysis for $C_{21}H_{20}NO_3Cl$: Calc. (%): C, 68.20; H, 5.45; N, 3.79; Found (%): C, 68.04; H, 5.47; N, 3.82.

Example 79'

To a solution of 4-(4-chlorophenyl)-2-oxazolepropionic acid (0.4 g) in THF (20 ml) were added triethylamine (0.33 ml) and ethyl chlorocarbonate (0.23 ml) at −30° C., followed by stirring for 30 minutes at the same temperature. The mixture was poured into 30% methylamine aqueous solution (10 ml), and the resultant was stirred for 15 minutes at room temperature. The reaction mixture was poured into water and extracted with ethyl acetate. The ethyl acetate layer was washed with water, dried over $MgSO_4$. The solvent was distilled off to give crystals of N-methyl-4-(4-chlorophenyl)-2-oxazolepropion-amide (0.375 g, 89%). Recrystallization from dichloromethane-ethanol gave colorless prism crystals of mp 169°–170° C.

Elementary analysis for $C_{13}H_{13}N_2O_2Cl$: Calc. (%): C, 58.99; H, 4.95; N, 10.58; Found (%): C, 58.73; H, 4.84; N, 10.46.

Example 80'

By the method of Example 79', crystals of N-benzyl-N-methyl-4-(4-chlorophenyl)-2-oxazolepropionamide (yield: 71%) were obtained. Recrystallization from dichloromethane-ethanol gave colorless prism crystals of mp 99°–100° C.

Elementary analysis for $C_{20}H_{19}N_2O_2Cl$: Calc. (%): C, 67.70; H, 5.40; N, 7.89; Found (%): C, 67.82; H, 5.38; N, 7.84.

Example 81'

To a solution of 4-(4-chlorophenyl)-2-oxazolepropionic acid (1.5 g) in THF (20 ml) was added lithium aluminum hydride (0.27 g), followed by stirring for 3 hours at room temperature. Water (3 ml) was added to the reaction mixture. The resultant was extracted with ethyl acetate. The ethyl acetate layer was washed with 2N-HCl and water, dried over $MgSO_4$, and distilled to remove the solvent. The oily residue was subjected to a silica gel chromatography. Crystals of 3-[4-(4-chlorophenyl)-2-oxazolyl]propanol (1.11 g, 78%) were obtained from the fraction eluted with ethyl acetate-hexane (2:1, V/V). Recrystallization from ether-hexane gave colorless prism crystals of mp 43°–44° C.

Elementary analysis for $C_{12}H_{12}NO_2Cl$: Calc. (%): C, 60.64: H, 5.09: N, 5.89: Found (%): C, 60.44; H, 5.06; N, 5.82.

Examples 82'–85'

By the method of Example 81', the compounds listed in Table 9' were obtained.

Example 86'

To a solution of ethyl 4-phenyl-2-oxazolepropionate (1.4 g) in THF (20 ml) was added sodium borohydride (0.86 g). Methanol (4 ml) was dropwise added to the mixture over a period of 10 minutes under reflux. The reaction mixture was refluxed for further 30 minutes, concentrated, made acidic and then extracted with ethyl acetate. The ethyl acetate layer was washed with water, dried over $MgSO_4$ and distilled to obtain crystals of 3-(4-phenyl-2-oxazolyl)propanol (1.07 g, 92%). Recrystallization from ether-hexane gave colorless prism crystals of mp 55°–56° C.

Elementary analysis for $C_{12}H_{13}NO_2$: Calc. (%): C, 70.92; H, 6.45; N, 6.89: Found (%): C, 70.65; H, 6.35; N, 6.67.

Examples 87'-88'

By the same manner as in Example 86', the compounds listed in Table 10' were obtained.

Example 89'

To a solution of 3-[4-(4-chlorophenyl)-2-oxazolyl]-propanol (1.0 g) in dichloromethane (10 ml) were added dimethylsulfoxide (0.6 ml) and phosphoric anhydride (1.1 g) in that order. After stirring for 10 minutes at room temperature, the resultant was cooled to 0° C., to which triethylamine (2 ml) was added. The mixture was stirred for 40 minutes at room temperature, poured into 2N-HCl and extracted with dichloromethane. The dichloromethane layer was washed with water, dried over MgSO₄ and distilled to remove the solvent. The oily residue was subjected to a silica gel column chromatography. Crystals of 3-[4-(4-chlorophenyl)-2-oxazolyl]propanol (0.698 g, 70%) were obtained from the fraction eluted with ethyl acetate-hexane (1:3, V/V). Recrystallization from hexane gave colorless prism crystals of mp 41°-42° C.

Elementary analysis for $C_{12}H_{10}NO_2Cl$: Calc. (%): C, 61.16; H, 4.28; N, 5.94; Found (%): C, 61.10; H, 4.21; N, 5.91.

Example 90'

To a solution 3-[4-(4-chlorophenyl)-2-oxazolyl]-propanol (0.5 g) in pyridine (5 ml) was added acetic anhydride (1.0 ml), followed by stirring for 30 minutes at 50° to 60° C. The reaction mixture was poured into water. The precipitated crystals were collected by filtration to obtain 3-[4-(4-chlorophenyl)-2-oxyazolyl]propyl acetate (0.535 g, 91%). Recrystallization from ether-hexane gave colorless prism crystals of mp 37°-37.5° C.

Elementary analysis for $C_{14}H_{14}NO_3Cl$: Calc. (%):C, 60.11; H, 5.04; N, 5.01; Found (%): C, 60.12; H, 5.06; N, 5.18.

Example 91'

To a solution of 3-[4-(4-chlorophenyl)-2-oxazolyl]-propanol (0.5 g) in pyridine (2 ml) was added benzoyl chloride (0.29 ml), followed by stirring for an hour at room temperature. The reaction mixture was poured into water and extracted with ethyl acetate. The ethyl acetate layer was washed succesively with an aqueous sodium hydrogen carbonate solution, 2N-HCl and water, dried over MgSO₄ and distilled to remove the solvent. The precipitated crystals were collected by filtration to give 3-[4-(4-chlorophenyl)-2-oxazolyl]propyl benzoate (0.687 g, 96%). Recrystallization from ether-hexane gave colorless prism crystals of mp 47°-47.5° C.

Elementary analysis for $C_{14}H_{14}NO_3Cl$: Calc. (%): C, 66.77; H, 4.72; N, 4.10; Found (%): C, 66.72; H, 4.70; N, 3.98.

Example 92'

To a solution of 3-[4-(4-chlorophenyl)-2-oxazolyl]-propanol (0.6 g) in DMF (10 ml) were added 60% (W/W) sodium hydride in oil (0.12 g) and benzyl bromide (0.3 ml), followed by stirring for 3 hours at room temperature. After additional stirring for an hour at 30° C., the reaction mixture was poured into water and then extracted with ether. The ether layer was washed with water, dried over MgSO₄ and distilled to remove the solvent. The oily residue was subjected to a silica gel column chromatography. Oily 3-[4-(4-chlorophenyl)-2-oxazolyl]propyl benzyl ether (0.512 g, 62%) was obtained from the fraction eluted with ether-hexane (1:4, V/V).

NMR (δppm, CDCl₃): 1.9-2.3(2H, m), 2.93(2H, t, J=7.5Hz), 3.57(2H, t, J=6.5 Hz), 4.52(2H, s), 7.35(5H, s), 7.37(2H, d, J=9Hz, 7.67(2H, d, J=9Hz), 7.80(1H, s).

Elementary analysis for $C_{19}H_{18}NO_2Cl$: Calc. (%): Cm 69.62; H, 5.53; N, 4.27; Found (%): C, 69.84; H, 5.48; N, 4.03;

Example 93'

3-[4-(4-Chlorophenyl)-2-oxazolyl]propanol (5.21 g) and triethylamine (4 ml) were dissolved in dichloromethane (50 ml), to which methanesulfonyl chloride (2.2 ml) was dropwise added under ice-cooling and stirred for 2 hours at the same temperature. The reaction mixture was poured into water and then extracted with dichloromethane. The dichloromethane layer was washed with water, dried over MgSO₄ and distilled to remove the solvent. The oily residue was dissolved in acetone (100 ml), to which sodium iodide (6.6 g) was added and refluxed for 2 hours. The solvent was distilled off. The residue was poured into water and extracted with ether. The ether layer was washed with an aqueous Na₂SO₃ solution and then water, and dried over MgSO₄. The solvent was distilled off to obtain 4-(4-chlorophenyl)-2-(3-iodopropyl)oxazole (6.6 g, 87%). Recrystallization from ether-hexane gave colorless prisms of mp 49°-50° C.

Elementary analysis for $C_{12}H_{11}NOClI$: Calc. (%): C, 41.47; H, 3.19; N, 4.03; Found (%): C, 41.46; H, 3.06; N, 4.03.

Example 94'

A mixture of 4-(4-chlorophenyl)-2-(3-iodopropyl)oxazole (0.5 g), guaiacol (0.19 ml), potassium carbonate (0.24 g) and N,N-dimethylformamide (5 ml) was stirred for 30 minutes at 60° to 65° C. and poured into water. precipitated crystals were collected by filtration to obtain 4-(4-chlorophenyl)-2-[3-(2-methoxyphenoxy) propyl]oxazole (0.445 g, 90%). Recrystallization from ether-hexane gave colorless prisms of mp 94°-95° C.

Elementary analysis for $C_{19}H_{18}NO_3Cl$: Calc. (%): C, 66.38; H, 5.28; N, 4.07; Found (%): C, 66.01; H, 5.20; N, 3.96.

Examples 95'-99'

By the method of Example 94', the compounds listed in Table 11' were obtained.

Preparation Example 1'

Tablet

Components of a tablet

| | |
|---|---:|
| (1) Compound (as obtained by Example 89') | 50 mg |
| (2) Cornstarch | 30 mg |
| (3) Lactose | 113.4 mg |
| (4) Hydroxypropyl cellulose | 6 mg |
| (5) Water | (0.03 ml) |
| (6) Magnesium stearate | 0.6 mg |
| Total | 200 mg |

The components (1), (2), (3) and (4) were mixed. After adding water, the mixture was kneaded, dried under vacuum for 16 hours at 40° C. and grounded in a mortar. The resultant was sieved through a 16-mesh sieve to obtain granules. The component (6) was added to the granules and mixed. The resulting mixture was made to tablets of 200 mg per tablet, using a rotary-type tablet machine (Kikusui Seisakusho in Japan).

Preparation Example 2'

| (1) Compound (as obtained by Example 81) | 50 mg |
|---|---|
| (2) Cornstarch | 30 mg |
| (3) Lactose | 113.4 mg |
| (4) Hydroxy-propyl cellulose | 6 mg |
| (5) Water | (0.03 ml) |
| (6) Magnesium stearate | 0.6 mg |
| (7) Cellulose acetate phthalate | 10 mg |
| (8) Acetone | (0.2 ml) |
| Total | 210 mg |

From the components (1), (2), (3), (4), (5) and (6), tablets were prepared by the same method as in Preparation Example 1. These tablets were film-coated by use of a solution of the component (7) in acetone in a half coater (Freunt Co., Ltd) to give entric tablets of 210 mg per tablet.

Preparation Example 3'

Components of a capsule

| (1) Compound C (as obtained by Example 64') | 30 mg |
|---|---|
| (2) Cornstarch | 40 mg |
| (3) Lactose | 74 mg |
| (4) Hydroxypropyl cellulose | 6 mg |
| (5) Water | 0.02 mg |
| Total | 150 mg |

The components (1), (2), (3) and (4) were mixed, to which water was added. The mixture was kneaded, dried under vacuum for 16 hours at 40° C. and grounded in a mortar. The resultant was sieved through a 16-mesh sieve to obtain granules. The granules were packed in No. 3 gelatin capsules with a capsule packing machine Zanasi Italy) to obtain capsules.

Preparation Example 4'

| (1) Compound (as obtained by Example 35') | 5 mg |
|---|---|
| (2) Sodium salicylate | 50 mg |
| (3) Sodium chloride | 180 mg |
| (4) Sodium metabisulfite | 20 mg |
| (5) Methylparaben | 36 mg |
| (6) Propylparaben | 4 mg |
| (7) Distilled water for injection | (2 ml) |
| Total | 295 mg |

The components (2), (3), (4), (5) and (6) were dissolved in about one half of the above mentioned volume of distilled water under stirring at 80° C. The solution thus obtained was cooled to 40° C., to which the compound of the present invention was dissolved. The remaining distilled water was added to the solution so that a final volume can be obtained. The resultant was sterilized through an appropriate filter paper, to obtain the injection.

(d) Effect of the Invention

From the results shown by the above Test Examples, the compounds (I'') or (I''') of the present invention have bone-reduction inhibitory action and bone-increase action in mammals (for example, mouse, rat, rabbit, dog, cat, bovine, swine, human, etc.) and in addition have low toxicity.

Accordingly, the compounds (I'') and (I''') of the present invention or salts thereof can be used for a therapeutic agent remedy for metabolic bone disease.

TABLE 3'

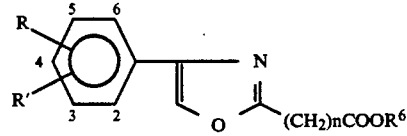

| No. of Examples | R, R' | $R^6$ | n | Yield (%) | MP (°C.) | Solvent for recrystallization |
|---|---|---|---|---|---|---|
| 2' | H, H | $C_2H_5$ | 2 | 60 | Oil[note 1] | — |
| 3' | 3-Cl, 4-Cl | $C_2H_5$ | 2 | 59 | 65–66 | Ether-hexane |
| 4' | 3-F, 4-F | $C_2H_5$ | 2 | 67 | Oil[note 2] | — |
| 5' | 4-CN, H | $C_2H_5$ | 2 | 53 | 66–67 | Ether-hexane |
| 6' | 4-$CF_3$, H | $C_2H_5$ | 2 | 64 | 63–63 | Ether-hexane |
| 7' | 4-$NO_2$, H | $C_2H_5$ | 2 | 60 | 97–98 | Acetone-hexane |
| 8' | 4-$OCHF_2$, H | $C_2H_5$ | 2 | 59 | 60–61 | Ether-hexane |
| 9' | 4-$OCF_3$, H | $C_2H_5$ | 2 | 62 | 36–37 | Hexane |
| 10' | 4-$CH_3$, H | $C_2H_5$ | 2 | 63 | Oil[note 3] | — |
| 11' | 3-$NO_2$, H | $C_2H_5$ | 2 | 56 | 76–77 | Ether-hexane |
| 12' | 2-Cl, 4-Cl | $C_2H_5$ | 2 | 70 | Oil[note 4] | — |
| 13' | 4-$C_2H_5$, H | $C_2H_5$ | 2 | 58 | Oil[note 5] | — |
| 14' | 3-$CF_3$, H | $C_2H_5$ | 2 | 36 | 60–61 | Ether-hexane |
| 15' | 2-$CF_3$, H | $C_2H_5$ | 2 | 34 | Oil[note 6] | — |
| 16' | 3-$NO_2$, 4-Cl | $C_2H_5$ | 2 | 72 | 65–66 | Ether-hexane |
| 17' | 2-Cl, 4-$NO_2$ | $C_2H_5$ | 2 | 48 | 71–72 | Ether-hexane |
| 18' | H, 4-Cl | $CH_3$ | 3 | 65 | 70–71 | Ether-hexane | note 1) NMR(δ ppm, $CDCl_3$): 1.25(3H, t, J=7.5Hz), 2.7–3.3(4H, m), 4.17(2H, q, J=7.5Hz), 7.2–7.55(3H, m), 7.6–7.8(2H, m), 7.81(1H, s).
note 2) NMR(δ ppm, $CDCl_3$): 1.25(3H, t, J=7.5Hz), 2.7~3.3(4H, m), 4.17(2H, q, J=7.5Hz), 6.95~7.3(3H, m), 7.77(1H, s).
note 3) NMR(δ ppm, $CDCl_3$): 1.24(3H, t, J=7.5Hz), 2.34(3H, s), 2.7–3.3(4H, m), 4.16(2H, q, J=7.5Hz), 7.17(2H, d, J=8.5Hz), 7.57(2H, d, J=8.5Hz), 7.75(1H, s).
note 4) NMR(δ ppm, $CDCl_3$): 1.24(3H, t, J=7.0Hz), 2.7–3.3(4H, m), 4.15(2H, q, J=7.0Hz), 7.2–7.5(2H, m), 8.05(1H, d, J=9.0Hz), 8.23(1H, s).
note 5) NMR(δ ppm, $CDCl_3$): 1.24(6H, t, J=7.0Hz), 2.5–3.3(6H, m), 4.15(2H, q, J=7.0Hz), 7.22(2H, d, J=9.0Hz), 7.62(2H, d, J=9.0Hz), 7.77(1H, s).
note 6) NMR(δ ppm, $CDCl_3$): 1.26(3H, t, J=7.0Hz), 2.7–3.3(4H, m), 4.18(2H, q, J=7.0Hz), 7.3–8.1(5H, m).

TABLE 4'

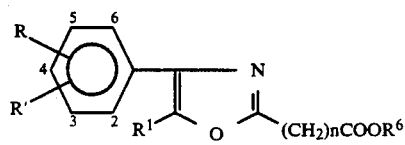

| No. of Examples | R, R' | $R^1$ | $R^6$ | n | Yield (%) | MP (°C.) | Solvent for recrystallization |
|---|---|---|---|---|---|---|---|
| 20' | H, 4-Cl | $CH_3$ | $CH_3$ | 3 | 67 | 52–53 | Ether-hexane |

TABLE 4'-continued

| No. of Examples | R, R' | R¹ | R⁶ | n | Yield (%) | MP (°C.) | Solvent for recrystallization |
|---|---|---|---|---|---|---|---|
| 21' | H, 4-Cl | $CH_3$ | $CH_3$ | 4 | 65 | 49–50 | Ether-hexane |
| 22' | H, 4-Cl | $CH_3$ | $C_2H_5$ | 6 | 63 | Oil[note 1)] | — |
| 23' | H, 4-Br | $CH_3$ | $C_2H_5$ | 2 | 67 | Oil[note 2)] | — |
| 24' | H, 4-F | $CH_3$ | $C_2H_5$ | 2 | 64 | Oil[note 3)] | — |
| 25' | H, 3-Cl | $CH_3$ | $C_2H_5$ | 2 | 50 | 44–45 | Hexane |
| 26' | H, 4-$\bigcirc$-$CH_2O$— | $CH_3$ | $C_2H_5$ | 2 | 67 | 59–59.5 | Ether-hexane |
| 27' | H, 4-$CF_3$ | $CH_3$ | $C_2H_5$ | 2 | 60 | Oil[note 4)] | — |
| 28' | H, 4-$CF_3O$— | $CH_3$ | $C_2H_5$ | 2 | 93 | Oil[note 5)] | — |

[note 1)]NMR(δ ppm in $CDCl_3$): 1.23(3H, t, J=7.0Hz), 1.1–2.0(8H, m), 2.28(3H, t, J=7.0Hz), 2.46(3H, s), 2.73(2H, t, J=7.0Hz), 4.12(2H, q, J=7.0Hz), 7.34(2H, d, J=9.0Hz), 7.56(H, d, J=9.0Hz).
[note 2)]NMR(δ ppm in $CDCl_3$): 1.25(3H, t, J=7.0Hz), 2.47(3H, m), 2.65–3.25(4H m), 4.16(2H, q, J=7.0Hz), 7.52(4H, s).
[note 3)]NMR(δ ppm in $CDCl_3$): 1.25(3H, t, J=7.0Hz), 2.47(3H, s), 2.65–3.2(4H, m), 4.17(2H, q, J=7.0Hz), 6.95–7.3(2H, m), 7.5–7.75(2H, m).
[note 4)]NMR(δ ppm in $CDCl_3$): 1.25(3H, t, J=7.0Hz), 2.53(3H, s), 2.7–3.3(4H, m), 4.17(2H, q, J=7.0Hz), 7.55–7.85(4H, m).
[note 5)]NMR(δ ppm in $CDCl_3$): 1.25(3H, t, J=7.0Hz), 2.48(3H, s), 2.65–3.2(4H, m), 4.17(2H, q, J=7.0Hz), 7.25(2H, d, J=9.0Hz), 7.66(2H, d, J=9.0Hz).

TABLE 5'

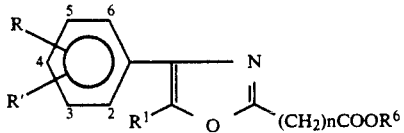

| No. of Examples | R, R' | R¹ | R⁶ | n | Yield (%) | MP (°C.) | Solvent for recrystallization |
|---|---|---|---|---|---|---|---|
| 30' | H, 4-Cl | $CH_3$ | $C_2H_5$ | 0 | 72 | 89–90 | Ethanol |
| 31' | H, 4-Cl | $CH_3$ | $C_2H_5$ | 2 | 69 | Oil[note 1)] | — |

TABLE 5'-continued

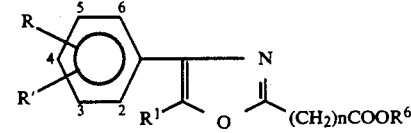

| No. of Examples | R, R' | R¹ | R⁶ | n | Yield (%) | MP (°C.) | Solvent for recrystallization |
|---|---|---|---|---|---|---|---|
| 32' | H, 4-Cl | $C_2H_5$ | $C_2H_5$ | 2 | 74 | Oil[note 2)] | — |

[note 1)]NMR(δ ppm in $CDCl_3$): 1.25(3H, t, J=7.5Hz), 2.46(3H, s), 2.7–3.2(4H, m), 4.16(2H, q, J=7.5Hz), 7.33(2H, d, J=9.0Hz), 7.55(2H, d, J=9.0Hz).
[note 2)]NMR(δ ppm in $CDCl_3$): 1.25(3H, t, J=7.5Hz), 1.27(3H, t, J=7.5Hz), 2.6–3.2(6H, m), 4.17(2H, q, J=7.5Hz), 7.35(2H, d, J=8.5Hz), 7.54(2H, d, J=8.5Hz).

TABLE 6'

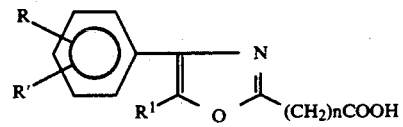

| No. of Examples | R, R' | R¹ | n | Yield (%) | MP (°C.) | Solvent for recrystallization |
|---|---|---|---|---|---|---|
| 34' | H, H | H | 2 | 67 | 119–120 | Ether-hexane |
| 35' | 4-Cl, H | H | 2 | 92 | 137–138 | Acetone-hexane |
| 36' | 3-Cl, 4-Cl | H | 2 | 83 | 126–127 | Acetone-hexane |
| 37' | 3-F, 4-F | H | 2 | 94 | 119–120 | Ether-hexane |
| 38' | 4-CN, H | H | 2 | 82 | 167–168 | Acetone-hexane |
| 39' | 4-$NO_2$, H | H | 2 | 87 | 180–181 | Acetone-hexane |
| 40' | 4-$CF_3$, H | H | 2 | 78 | 151–152 | Acetone-hexane |
| 41' | 4-$OCHF_2$, H | H | 2 | 73 | 108–109 | Ether-hexane |
| 42' | 4-$OCF_3$, H | H | 2 | 78 | 118–119 | Ether-hexane |
| 43' | 4-$CH_3$, H | H | 2 | 79 | 128–129 | Acetone-hexane |
| 44' | 3-$NO_2$, H | H | 2 | 89 | 152–153 | Acetone-hexane |
| 45' | 2-Cl, 4-Cl | H | 2 | 85 | 137–138 | Acetone-hexane |
| 46' | 4-$C_2H_5$, H | H | 2 | 80 | 123–124 | Ether-hexane |

TABLE 6'-continued

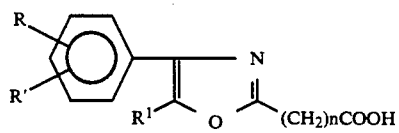

| No. of Examples | R, R' | $R^1$ | n | Yield (%) | MP (°C.) | Solvent for recrystallization |
|---|---|---|---|---|---|---|
| 47' | 3-CF$_3$, H | H | 2 | 93 | 93-94 | Ether-hexane |
| 48' | 2-CF$_3$, H | H | 2 | 91 | 55-56 | Ether-hexane |
| 49' | 3-NO$_2$, 4-Cl | H | 2 | 85 | 186-187 | Acetone-hexane |
| 50' | 2-Cl, 4-NO$_2$ | H | 2 | 92 | 156-157 | Acetone-hexane |
| 51' | H, 4-Cl | CH$_3$ | 0 | 89 | 102-103 | Ethanol-water |
| 52' | H, 4-Cl | CH$_3$ | 2 | 93 | 133-134 | Ether-hexane |
| 53' | H, 4-Cl | C$_2$H$_5$ | 2 | 91 | 175-176 | Acetone-hexane |
| 54' | H, 4-Cl | H | 3 | 85 | 107-108 | Acetone-hexane |
| 55' | H, 4-Cl | CH$_3$ | 3 | 88 | 101-102 | Ether-hexane |
| 56' | H, 4-Cl | CH$_3$ | 6 | 90 | 88-89 | Ether-hexane |
| 57' | H, 4-Br | CH$_3$ | 2 | 91 | 166-167 | Ethanol-ether |
| 58' | H, 4-F | CH$_3$ | 2 | 85 | 113-113.5 | Ether-hexane |
| 59' | H, 3-Cl | CH$_3$ | 2 | 57 | 92-93 | Acetone-hexane |
| 60' | H, 4-⌬-CH$_2$O— | CH$_3$ | 2 | 88 | 141-142 | Ethanol |
| 61' | H, 4-CF$_3$ | CH$_3$ | 2 | 88 | 129-130 | Acetone-hexane |
| 62' | H, 4-CF$_3$O | CH$_3$ | 2 | 82 | 72-73 | Ethanol-hexane |

TABLE 7'

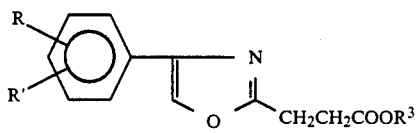

| No. of Examples | R, R' | $R^3$ | Yield (%) | MP (°C.) | Solvent for recrystallization |
|---|---|---|---|---|---|
| 65' | H, 4-Cl | naphthyl-CH$_2$— | 92 | 69-70 | Ether-hexane |
| 66' | H, 4-Cl | 2,6-dichlorobenzyl-CH$_2$— | 89 | 62-63 | Ether-hexane |
| 67' | H, 4-Cl | cyclohexyl | 90 | 37-38 | Ether-hexane |
| 68' | H, 4-Cl | —CH$_2$CH$_2$N(CH$_3$)$_2$ · HCl | 85 | 160-161 | Dichloromethane-ethanol |
| 69' | H, 4-Cl | —CH$_2$—C$_6$H$_4$—Cl | 89 | 77-78 | Ether-hexane |

TABLE 7'-continued

Structure: R,R'-substituted phenyl—CH=CH—O—C(=N)—CH₂CH₂COOR³ (oxazoline)

| No. of Examples | R, R' | R³ | Yield (%) | MP (°C.) | Solvent for recrystallization |
|---|---|---|---|---|---|
| 70' | H, 4-Cl | —CH(Me)—phenyl | 76 | 52–53 | Ether-hexane |
| 71' | H, 4-Cl | —CH₂—(2-methylphenyl) | 73 | 47–48 | Ether-hexane |
| 72' | H, 4-Cl | —CH₂—(4-methoxyphenyl) | 99 | 69–70 | Ether-hexane |

TABLE 8'

Structure: R,R'-substituted phenyl—CH=CH—O—C(=N)—CH₂CH₂COOR³

| No. of Examples | R, R' | R³ | Yield (%) | MP (°C.) | Solvent for recrystallization |
|---|---|---|---|---|---|
| 74' | H, 4-Cl | cyclohexyl | 54 | 38–39 | Hexane |
| 75' | H, 4-Cl | geranyl (CH₂—) | 73 | Oil[note 1] | — |
| 76' | H, 4-Cl | —CH₂—(2-OCH₃,4-OCH₃-phenyl) | 61 | 72–72 | Dichloromethane-hexane |

[note 1] NMR(δ ppm, CDCl₃): 1.59(3H, s), 1.68(6H, s), 1.95–2.2(4H, m), 2.7~3.3(4H, m), 4.64(2H, d, J=7Hz), 5.08(1H, bs), 5.34(1H, bt, J=7Hz), 7.34(2H, d, J=9Hz), 7.64(2H, d, J=9Hz), 7.80(1H, s).

TABLE 9'

Structure: R,R'-substituted phenyl—CH=CH—O—C(=N)—CH₂CH₂CH₂OH

| No. of Examples | R, R' | Yield (%) | MP (°C.) | Solvent for recrystallization |
|---|---|---|---|---|
| 82' | H, 4-CH₃ | 73 | 41–42 | Ether-hexane |
| 83' | H, 4-CF₃ | 82 | 61–61.5 | Ether-hexane |
| 84' | H, 4-NO₂ | 38 | 86–87 | Dichloromethane-hexane |
| 85' | H, 4-OCF₃ | 78 | 77–78 | Ether-hexane |

TABLE 10'

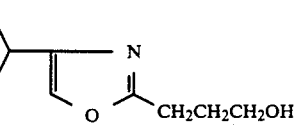

| No. of Examples | R, R' | Yield (%) | MP (°C.) | Solvent for recrystallization |
|---|---|---|---|---|
| 87' | H, 4-OCHF$_2$ | 98 | 56–57 | Ether-hexane |
| 88' | H, 4-CN | 65 | 101–102 | Dichloromethane-hexane |

TABLE 11'

| No. of Examples | R, R' | R$^2$ | Yield (%) | MP (°C.) | Solvent for recrystallization |
|---|---|---|---|---|---|
| 95' | H, 4-Cl | phenyl | 78 | 99–100 | Ether-hexane |
| 96' | H, 4-Cl | C$_2$H$_5$O-phenyl | 71 | 56–57 | Ether-hexane |
| 97' | H, 4-Cl | CH$_3$O, CH$_3$O-phenyl | 61 | 66–67 | Ether-hexane |
| 98' | H, 4-Cl | CH$_3$CO-phenyl | 82 | 79–80 | Ether-hexane |
| 99' | H, 4-Cl | CH$_3$OOC-phenyl | 85 | Oil$^{note\ 1)}$ | — |

$^{note\ 1)}$NMR($\delta$ ppm, CDCl$_3$): 2.15–2.5(2H, m), 3.08(2H, t, J=7.5Hz), 3.87(3H, s), 4.17(2H, t, J=6.0Hz), 6.85–7.1(2H, m), 7.2–7.9(7H, m).

What we claimed is:

1. An oxazole compound having the formula (I):

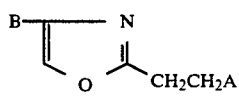

in which A is a group of the formula —CH$_2$OR$^3$ wherein R$^3$ is a phenyl, napthyl, anthryl or phenanthryl group which is unsubstituted or substituted by one to three substituents, which may be the same or different, selected from the group consisting of (1) halogen; (2) hydroxy; (3) C$_{1-6}$ alkoxy or (4) C$_{1-10}$ acyl, formed from a C$_{1-10}$ alkyl, phenyl C$_{1-4}$ alkyl, C$_{2-10}$ alkenyl, phenyl, napthyl or phenanthryl group and a carbonyl or sulfonyl group; or A is an aldehyde group; and B is a phenyl group which is unsubstituted or substituted by one to four substituents, which may be the same or different, selected from the group consisting of halogen, nitro, cyano, a C$_{1-10}$ alkoxy group which is unsubstituted or substituted by one to three substituents, which may be the same or different, wherein said substituents for said alkoxy and said alkyl groups are selected from the group consisting of halogen, hydroxy and C$_{1-6}$ alkoxy;

or a pharmaceutically acceptable salt thereof.

2. A compound of claim 1, wherein R$^3$ is a phenyl, napthyl, anthryl or phenanthryl group, or a pharmaceutically acceptable salt thereof.

3. A compound of claim 1, wherein R$^3$ is a phenyl, napthyl, anthryl or phenanthryl group which is substituted by one to three halogen atoms, or a pharmaceutically acceptable salt thereof.

4. A compound of claim 1, wherein R$^3$ is a phenyl, napthyl, anthryl or phenanthryl group which is substituted by one to three hydroxyl groups, or a pharmaceutically acceptable salt thereof.

5. A compound of claim 1, wherein $R^3$ is a phenyl, napthyl, anthryl or phenanthryl group which is substituted by one to three $C_{1-6}$ alkoxy groups, or a pharmaceutically acceptable salt thereof.

6. A compound of claim 1, wherein $R^3$ is a phenyl, napthyl, anthryl or phenanthryl group which is substituted by one to three $C_{1-10}$ acyl groups, or a pharmaceutically acceptable salt thereof.

7. A compound which is 3-(4-(4-chlorophenyl)-2-oxazolyl)propyl benzoate.

* * * * *